United States Patent
Thor et al.

(10) Patent No.: US 12,053,406 B2
(45) Date of Patent: *Aug. 6, 2024

(54) FOOT ANKLE ORTHOSIS

(71) Applicant: AST DESIGN LLC, Coronado, CA (US)

(72) Inventors: Arni Thor, San Diego, CA (US); Shireen Thor, San Diego, CA (US)

(73) Assignee: AST Design, LLC, Coronado, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,298

(22) Filed: Oct. 31, 2022

(65) Prior Publication Data
US 2023/0117491 A1    Apr. 20, 2023

Related U.S. Application Data

(63) Continuation of application No. 15/977,880, filed on May 11, 2018, now Pat. No. 11,484,426.

(60) Provisional application No. 62/505,740, filed on May 12, 2017, provisional application No. 62/625,893, filed on Feb. 2, 2018.

(51) Int. Cl.
*A61F 5/01* (2006.01)
*A43B 7/20* (2006.01)
*A61F 13/08* (2006.01)

(52) U.S. Cl.
CPC .............. *A61F 5/0113* (2013.01); *A43B 7/20* (2013.01); *A61F 13/08* (2013.01); *A61F 5/0127* (2013.01)

(58) Field of Classification Search
CPC ........ A61F 5/01; A61F 5/0102; A61F 5/0104; A61F 5/0109; A61F 5/0111; A61F 5/0113; A61F 5/0118; A61F 5/0127; A61F 5/013; A61F 13/06; A61F 13/064; A61F 13/066; A61F 13/08; A61F 13/085; A43B 7/20

See application file for complete search history.

(56) References Cited

U.S. PATENT DOCUMENTS

| 2,949,111 A | 8/1960 | Ruotoistenmaki |
| 4,646,726 A | 3/1987 | Westin et al. |

(Continued)

FOREIGN PATENT DOCUMENTS

| EP | 0270661 | 6/1987 |
| EP | 2932944 | 10/2015 |

(Continued)

OTHER PUBLICATIONS

Written Opinion of the International Searching Authority for PCT/US2020/047228 dated Dec. 2, 2020.

*Primary Examiner* — Keri J Nelson
(74) *Attorney, Agent, or Firm* — Garson & Gutierrez, PC

(57) ABSTRACT

Methods and apparatus for human anatomical orthoses. In one embodiment, an orthoses is disclosed that has been integrated into a sock and includes a tensioning element that is configured to keep the top portion of the sock at or above a user's calf muscle, a rotary tensioning mechanism disposed adjacent to the top portion of the sock, a support cable that is weaved within the body of the sock such that the support cable is maintained in close proximity with a user's leg when tension is applied thereto, and a supporting structure that is coupled to the support cable, the supporting structure being disposed adjacent to a user's toes. Methods of manufacturing and using the aforementioned orthoses is also disclosed.

20 Claims, 37 Drawing Sheets

(56) References Cited

U.S. PATENT DOCUMENTS

| | | | |
|---|---|---|---|
| 5,776,090 | A | 7/1998 | Bergmann et al. |
| 5,817,041 | A | 10/1998 | Bader |
| 5,897,515 | A | 4/1999 | Willner et al. |
| 6,110,135 | A | 8/2000 | Madow et al. |
| 6,146,344 | A | 11/2000 | Bader |
| 6,146,349 | A | 11/2000 | Rothschild et al. |
| 6,676,618 | B2 | 1/2004 | Andersen |
| 6,945,947 | B2 | 9/2005 | Ingimundarson et al. |
| 7,077,818 | B2 | 7/2006 | Ingimundarson et al. |
| 7,266,910 | B2 | 9/2007 | Ingimundarson |
| 7,270,644 | B2 | 9/2007 | Ingimundarson |
| 7,354,413 | B2 | 4/2008 | Fisher |
| 7,513,880 | B2 | 4/2009 | Ingimundarson et al. |
| 7,749,423 | B2 | 7/2010 | Bader |
| 7,753,864 | B2 | 7/2010 | Beckwith et al. |
| 7,766,851 | B2 | 8/2010 | Lindh et al. |
| 8,021,316 | B2 | 9/2011 | Franke et al. |
| 8,323,224 | B2 | 12/2012 | Shlomovitz |
| 8,403,872 | B2 | 3/2013 | Franke et al. |
| 8,540,655 | B2 | 9/2013 | Franke et al. |
| 9,121,673 | B2 | 9/2015 | Popovici |
| 9,192,504 | B2 | 11/2015 | Andrews et al. |
| 9,211,208 | B2 | 12/2015 | Blum et al. |
| 9,326,880 | B2 | 5/2016 | Szczepanski |
| 9,433,522 | B2 | 9/2016 | Bader |
| 9,526,651 | B2 | 12/2016 | Kozasa et al. |
| 9,562,742 | B2 | 2/2017 | Popovici |
| 9,855,161 | B1 | 1/2018 | Bonaroti |
| 9,889,035 | B2 | 2/2018 | Jordan et al. |
| 9,901,475 | B2 | 2/2018 | Jordan et al. |
| 9,980,847 | B2 | 5/2018 | Andrews et al. |
| 10,052,221 | B2 | 8/2018 | Albertsson et al. |
| 10,105,252 | B2 | 10/2018 | Bader |
| 10,561,514 | B2 | 2/2020 | Romo et al. |
| 11,484,426 | B2 * | 11/2022 | Thor ................ A43B 7/20 |
| 2005/0234378 | A1 | 10/2005 | Ingimundarson et al. |
| 2007/0038169 | A1 | 2/2007 | Alon et al. |
| 2007/0073202 | A1 | 3/2007 | Bader |
| 2007/0100268 | A1 | 5/2007 | Fisher |
| 2008/0077066 | A1 | 3/2008 | Lewis |
| 2008/0300525 | A1 | 12/2008 | Shlomovitz |
| 2009/0287128 | A1 | 11/2009 | Ingimundarson et al. |
| 2013/0072841 | A1 | 3/2013 | Bader |
| 2013/0131569 | A1 | 5/2013 | Blum et al. |
| 2014/0276318 | A1 | 9/2014 | Faux |
| 2014/0276320 | A1 | 9/2014 | Faux et al. |
| 2014/0378881 | A1 | 12/2014 | Wagner |
| 2015/0065934 | A1 | 3/2015 | Bader |
| 2015/0119781 | A1 | 4/2015 | Ponce |
| 2015/0148725 | A1 | 5/2015 | Johnsson et al. |
| 2015/0150709 | A1 | 6/2015 | Ljubimir et al. |
| 2015/0265450 | A1 | 9/2015 | Rodgers |
| 2015/0320581 | A1 | 11/2015 | Causse |
| 2016/0074199 | A1 | 3/2016 | Bader |
| 2016/0213552 | A1 | 7/2016 | Lindsay |
| 2016/0220406 | A1 | 8/2016 | Bader |
| 2017/0165094 | A1 | 6/2017 | Voskuilen et al. |
| 2017/0165095 | A1 | 6/2017 | Romo et al. |
| 2017/0216071 | A1 | 8/2017 | Bader |
| 2017/0348132 | A1 | 12/2017 | Cooney |
| 2018/0333285 | A1 | 11/2018 | Thor et al. |

FOREIGN PATENT DOCUMENTS

| | | |
|---|---|---|
| EP | 3301680 | 9/2017 |
| GB | 2375962 | 12/2002 |
| GB | 25355612 | 8/2016 |
| GB | 2556317 | 5/2018 |
| GB | 2571963 | 9/2019 |
| GB | 2571965 | 9/2019 |
| RU | 2277394 | 6/2006 |
| WO | 2001034071 | 5/2001 |
| WO | 2004066890 | 8/2004 |
| WO | 2008001394 | 1/2008 |
| WO | 2009139019 | 11/2009 |
| WO | 2011029837 | 3/2011 |
| WO | 2014001793 | 1/2014 |
| WO | 2017103621 | 6/2017 |
| WO | 2017134429 | 8/2017 |
| WO | 2017207532 | 12/2017 |
| WO | 2017212242 | 12/2017 |
| WO | 2019175589 | 9/2019 |
| WO | 2019175592 | 9/2019 |

* cited by examiner

FOOT ANKLE ORTHOSIS

PRIORITY

This application is a continuation of, and claims the benefit of priority to, U.S. patent application Ser. No. 15/977,880 filed May 11, 2018 of the same title, which claims the benefit of priority to both co-owned and U.S. Provisional Patent Application Ser. No. 62/505,740 filed May 12, 2017 entitled "Methods and Apparatus for Human Anatomical Orthoses" and U.S. Provisional Patent Application Ser. No. 62/625,893 filed Feb. 2, 2018 entitled "Methods and Apparatus for Human Anatomical Orthoses", the contents of each of the foregoing being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE DISCLOSURE

Field of the Disclosure

The present disclosure relates generally to the field of the correction of disorders of the limbs or spine by use of braces and other devices to correct alignment or provide support and in one exemplary aspect, to foot and ankle orthoses and methods for manufacturing and using the same.

Description of Related Art

Drop foot is a common medical condition that has its source in various different pathological conditions. The condition may be caused by trauma in which the peroneal nerve that innervates the peroneal muscles becomes damaged. Drop foot may also be present following a stroke, or it may be congenital. Many orthotic treatments exist for the treatment of drop foot including, for example: rigid ankle foot orthoses (AFOs); semi-rigid foot orthoses; soft AFOs (such as "Foot Up"-type devices or a soft ankle brace with straps); and functional electrical stimulation systems.

The primary goal for each of these solutions is in the prevention of plantar flexion of the foot during swing phase, as well as reducing foot slap during heel strike. Considerations that these devices try to take into account are one or more of: (1) improved overall stability of the ankle; (2) the devices ease of use (i.e., easy to put on or take off); (3) the devices are comfortable to wear; (4) the devices are aesthetically pleasing in appearance; and/or (5) the devices are easy to wear with shoes. Unfortunately while these devices try to maximize one or more of the benefits listed above, most fail at achieving all of these items, or are otherwise sub-optimal in one or more of these areas. For example, typical complaints by patients with a drop foot condition that are mentioned when utilizing these prior orthopedic devices are: (1) the device is uncomfortable to wear; (2) the device is difficult to integrate into a standard shoe; (3) the device is too big and bulky; (4) the device typically needs to be worn with a specially designed shoe, which isn't always appropriate in all circumstances (e.g., when wearing the device at home); and (5) the device does not provide the proper amount of immobilization (i.e., too much or too little support) for everyday usage.

In recent years, there have been two (2) main types of devices which have particularly tried to tackle these five (5) common complaints; however these devices have not managed to solve these problems, or other problems have arisen as a result of their designs. One such type of device is a functional electrical stimulation device. While functional electrical stimulation devices are promoted as providing stability only when you need it; being low profile and generally easy to hide; are generally easy to put on and take off; and can be worn with or without shoes, these types of devices aren't without their drawbacks. For example, often times these functional electrical stimulation devices can be uncomfortable to wear; don't always work; and are relatively expensive. Another type of device are so-called "Foot Up" types of devices, that typically include a soft ankle strap that connects to a shoe or a foot strap. These types of devices are typically low profile and easy to hide; are easy to put on and take off; and are generally comfortable. However, these types of devices are not very aesthetically pleasing; offer poor support (e.g., the device slips down on a user's ankle and otherwise loses its ability to provide a supporting function); and preferably need to be worn with shoes.

Accordingly, despite the wide variety of the foregoing solutions, there remains a salient need for an orthotic device that: provides adequate support for everyday use; is comfortable to wear; is inexpensive; is easy to put on and take off; can be worn with and without shoes; and fits well with existing clothing.

SUMMARY

The present disclosure satisfies the foregoing needs by providing, inter alia, an orthoses apparatus for addressing each of the foregoing desirable traits as well as methods of their manufacture and methods of their use.

In one aspect of the present disclosure, an orthoses is disclosed. In one embodiment, the orthoses has been integrated into a sock and includes a tensioning element that is configured to keep the top portion of the sock at or above a user's calf muscle, a rotary tensioning mechanism disposed adjacent to the top portion of the sock, a support cable that is weaved within the body of the sock such that the support cable is maintained in close proximity with a user's leg when tension is applied thereto, and a supporting structure that is coupled to the support cable, the supporting structure being disposed adjacent to a user's toes.

In another embodiment, the orthoses may be configured for positioning around a joint of, for example, a human body. The orthoses may further include a tensioning element that is configured to apply flexion to the joint. In one variant, instead of applying flexion to the joint, the tensioning element may be configured to apply extension to the joint. In some variants, the joint may be one or more of joints on an arm (e.g., elbow, wrist, etc.), shoulder, and knee.

In another embodiment, the orthoses includes a foot ankle orthoses. In one variant, the foot ankle orthoses includes a sock that is configured to fit over a calf muscle on a leg of a user; and a compression strap system that includes: an upper retention structure that is configured to be positioned above the calf muscle of the user when disposed on the leg of the user, the upper retention structure including a first structure that is spaced circumferentially from a second structure; an ankle retention structure that is configured to be positioned around an ankle of the user and below the calf muscle of the user; a foot retention structure that is configured to be positioned proximate a ball of a foot of a user; and a support element that is operatively coupled with the first structure, the second structure, the ankle retention structure, and the foot retention structure. The upper retention structure is configured to tighten around an anatomy of the user when the sock moves into a plantar flexed position via application of tension between the first structure and the second structure.

In another variant, the ankle retention structure includes: an upper ankle retention structure that is configured to be positioned above the ankle of the user and below the calf muscle of the user; and a lower ankle retention structure that is configured to be positioned below the ankle of the user at a transition point between a heel of the user and a midfoot of the user.

In yet another variant, the support element includes one or more of a support strap or a support cable.

In yet another variant, an adjustable tensioning mechanism is disclosed that is disposed at an upper portion of the sock, the adjustable tensioning mechanism configured to tension the support strap or the support cable.

In yet another variant, the sock is separable from the compression strap system.

In yet another variant, the compression strap system is integrated with the sock.

In yet another variant, the upper retention structure is configured to tighten around an anatomy of the user when either: (i) the adjustable tensioning mechanism is tightened and/or (ii) the user's foot goes into plantar flexion.

In yet another variant, the upper ankle retention structure and the lower ankle retention structure is configured to tighten around the anatomy of the user when the adjustable tensioning mechanism is tightened.

In yet another variant, the foot retention structure is configured to place the foot of the user into a neutral to slight dorsiflexion when the adjustable tensioning mechanism is tightened.

In yet another variant, the sock includes low stretch in a horizontal direction at least in a region adjacent to the ankle of the user and in a region above the calf muscle of the user as compared with at least one other region of the sock.

In yet another variant, the support strap or the support cable comprises a substantially inelastic material.

In yet another variant, the sock includes one or more layers of material and the support strap or the support cable is threaded into and out of at least one of the one or more layers of material.

In yet another variant, one or more of the upper retention structure, the upper ankle retention structure, the lower ankle retention structure, and the foot retention structure is disposed internal to at least one of the one or more layers of material.

In yet another variant, the sock includes two or more layers of material and the support strap or the support cable is threaded between at least two of the two or more layers of material thereby preventing direct contact of the support strap or the support cable with skin of the user.

In yet another variant, one or more of the upper retention structure, the upper ankle retention structure, the lower ankle retention structure, and the foot retention structure is disposed internal to at least one of the two or more layers of material.

In yet another variant, the foot ankle orthoses further includes a plurality of support strap/cable guides that is configured to reduce friction and facilitate movement of the support strap or the support cable.

In yet another variant, a reinforced structure is disposed on a top portion of the foot of the user, the reinforced structure configured to prevent over tensioning of the support strap or the support cable in a region of the foot of the user.

In another aspect of the present disclosure, a method of manufacturing an orthoses is disclosed. In one embodiment, the method includes weaving a sock, the sock weaved such that the sock has minimal stretch in a horizontal direction adjacent to a top portion of the orthoses, the ankle region of the orthoses and the foot/toe region of the orthoses as well as in a vertical direction; attaching a connecting point adjacent to the foot/toe region of the orthoses; attaching a rotary tensioning dial adjacent the top portion of the orthoses; and weaving a supporting cable through the sock between the top portion of the orthoses and the connecting point disposed adjacent to the foot/toe region of the orthoses.

In yet another aspect of the present disclosure, a method of using an orthoses is disclosed. In one embodiment, the method includes placing a sock-based orthoses over the lower leg of a user; and applying tension to a support strap in order to place the user's foot into a neutral to slight dorsiflexion thereby limiting plantarflexion of the ankle.

In another embodiment, the method includes releasing tension to a support strap; and removing a sock-based orthoses from the lower leg of a user.

In yet another embodiment, the method includes placing a sock onto a leg of a user; pulling a top portion of the sock over a calf muscle on the leg of the user; and adjusting tension of a compression strap system of the sock, the adjusting of the tension of the compression strap system includes simultaneously: adjusting of tension between a first structure that is circumferentially spaced from a second structure, the first structure and the second structure being disposed on an upper retention structure; and adjusting tension between the upper retention structure and a foot retention structure.

In one variant, the pulling of the top portion of the sock over the calf muscle on the leg of the user includes pulling the upper retention structure over the calf muscle on the leg of the user.

In another variant, the adjusting of the tension of the compression strap system includes rotating a rotary tensioning mechanism in order to adjust tension of a support strap or a support cable that is operatively coupled with the upper retention structure, an ankle retention structure, and the foot retention structure.

Other features and advantages of the present disclosure will immediately be recognized by persons of ordinary skill in the art with reference to the attached drawings and detailed description of exemplary implementations as given below.

All Figures disclosed herein are © Copyright 2017-2018 AST Design, LLC. All rights reserved.

DETAILED DESCRIPTION

Implementations of the present technology will now be described in detail with reference to the drawings, which are provided as illustrative examples so as to enable those skilled in the art to practice the technology. Notably, the figures and examples below are not meant to limit the scope of the present disclosure to any single implementation or implementations, but other implementations are possible by way of interchange of, substitution of, or combination with some or all of the described or illustrated elements. Wherever convenient, the same reference numbers will be used throughout the drawings to refer to same or like parts.

Moreover, while embodiments described herein are primarily discussed in the context of foot and ankle orthoses for the treatment of drop foot, it will be recognized by those of ordinary skill that the present disclosure is not so limited. In fact, the principles of the present disclosure described herein may be readily applied to other parts of the anatomy of a human, and for treatment of conditions other than drop foot. For example, many common injuries, such as a partial or complete tear of a tendon (e.g., a biceps tendon, a triceps tendon, an Achilles tendon, and the like), may require an individual to rest the injured tendon, whether surgical or non-surgical treatment is required. Accordingly, the principles described herein may be readily adapted for use with other portions of the anatomy. For example, the drop foot sock devices described herein may be readily adapted for use on the arm, elbow, shoulder, knee (see, for example, FIG. 8D), etc. where movement, whether in extension or flexion, may need to be constrained in order to facilitate recovery from, for example, an injury or other medical condition.

Figure 1:
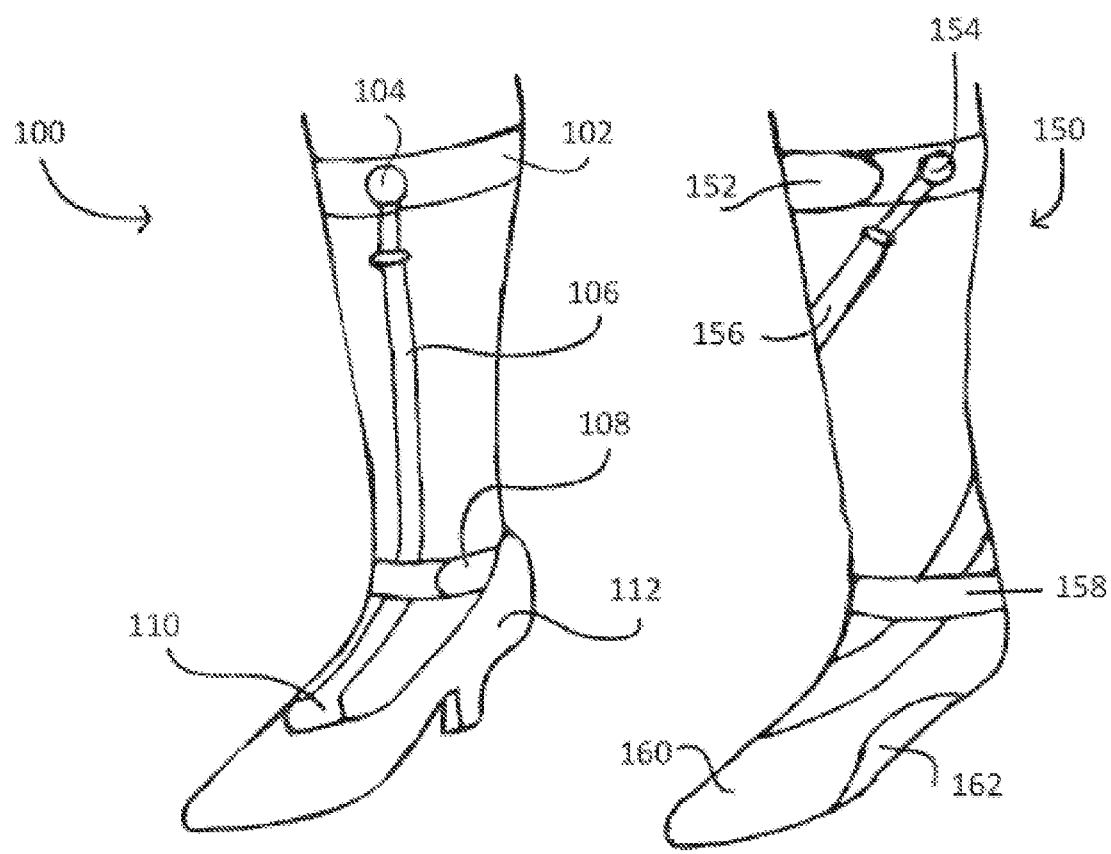
FIG. 1 is a front perspective view of two exemplary orthoses devices, in accordance with the principles of the present disclosure.

Referring now to FIG. 1, two foot-ankle orthoses 100, 150 are shown and described in detail. Foot-ankle orthoses 100 may include an adjustable strap 102 (e.g., Velcro) that is disposed at, for example, the top of the calf muscle. The disposition at the top of the calf muscle may be advantageous in some implementations as securing the strap 102 may prevent the top of the sock from being pulled down over the calf muscle when the support strap 106 is tightened. In some implementations, the adjustable strap 102 may be placed above the knee and/or at any other location on the anatomy of a subject (e.g., a human or animal) where the prevention of the adjustable strap 102 from being "pulled down" when under tension would be readily appreciated by one of ordinary skill given the contents of the present disclosure. For example, in some implementations it may be advantageous to include a first adjustable strap at the top of the calf muscle and a second adjustable strap just above the knee. In such a configuration, it may be advantageous to have the first and second adjustable straps joined together such as is common with many extant knee brace configurations.

In some implementations, the adjustable strap 102 may include a rotary tensioning dial 104 (e.g., a so-called BOA® tensioning system). As a brief aside, the rotary tensioning system may include a micro-adjustable dial, a strong lightweight lace or cable, and a low friction lace guide. Accordingly, by rotating the micro-adjustable dial, the rotary tensioning dial may apply tension to the support strap 106 thereby bringing the foot into, for example, a neutral to slight dorsiflexion thereby limiting plantarflexion of the ankle which may be advantageous in addressing, for example, a drop foot condition. By tightening the rotary tensioning dial 104, the support strap 106 that runs down the tibia may be tightened. Conversely, when loosening the rotatory tensioning dial 104 (e.g., by pulling the dial away from the base), the support strap 106 that runs down the tibia may be loosened. Moreover, in some implementations, the rotary tensioning dial 104 may be used to apply tension to support strap 106 as well as adjustable strap 102 simultaneously in a similar manner as is described with respect to FIG. 8B described infra. In other words, by tightening (or loosening) rotary tensioning dial 104 tension (or lack of tension) may be simultaneously applied to both support strap 106 as well as adjustable strap 102.

The support strap 106 may be secured at the ankle using an ankle strap 108. While the support strap 106 is depicted as running underneath the ankle strap 108, it would be readily appreciated by one of ordinary skill given the contents of the present disclosure that alternative configurations are readily recognized. For example, ankle strap 108 may include, for example, a low friction interface that may run through the middle of ankle strap 108. Alternatively, a low friction interface may be placed on the top surface of the ankle strap 108. As used herein, the term "low friction interface" shall mean an interface in which the tensioning (or loosening) of, for example, support strap 106 is not significantly impeded as a result of friction. Support strap 106 may continue over the dorsum of the foot where it is coupled to a supporting structure 110.

Supporting structure 110 (that may be implemented into a sock in some implementations) may allow for circumferential stretching as a means by which orthoses 100 remains comfortable to wear by a user. Supporting structure 110 may possess a more limited ability to stretch in the longitudinal direction (e.g., along the dorsum of the foot) in order to maintain, for example, an appropriate amount of tension when tension is applied (e.g., by pulling the ankle into dorsiflexion), thereby reducing the effects associated with the drop foot condition.

Foot ankle orthoses 150 may possess many of the same features described with respect to foot ankle orthoses 100. For example, orthoses 150 may include an adjustable strap 152, a rotary tensioning dial 154, a support strap 156, an ankle strap 158 as well as a supporting structure 160. However, the support strap 156 associated with orthoses 150 is configured to rotate around the calf, run over the dorsum of the foot, and anchor to the medial side of the foot. This type of a strapping configuration may both: (1) prevent plantar flexion, similar to that shown with respect to orthoses 100; and (2) reduce pronation, a common condition associated with the drop foot condition. Additionally, orthoses 150 may provide rotational control of the ankle and normalize the gait.

While the support strap 156 is illustrated as providing a single rotation about a user's tibia, it would be readily appreciated by one of ordinary skill given the contents of the present disclosure that two or more rotations about a user's tibia may be desirable in some implementations. Moreover, while support strap 156 is illustrated as being anchored to the medial side of the foot, in some implementations it may be desirable to be anchored to the lateral side of the foot, thereby reducing supination and normalizing the gait of the wearer of orthoses 150. Both of orthoses 100, 150 may be worn with or without a sock and both may also be worn with or without a shoe in some implementations. In the illustrated embodiment, the rotary tensioning dial 154 is shown as being disposed on the lateral side of the leg; however, in some implementations it may be desirable to position the rotary tensioning dial at the center of the leg (top portion of the shin), at the center of the leg above the calf, or it may be desirable to position the rotary tensioning dial on the medial side of the leg (such as when support strap 156 is anchored on the lateral side of the foot, etc.). These and other variations would be readily apparent to one of ordinary skill given the contents of the present disclosure.

Figure 1A:
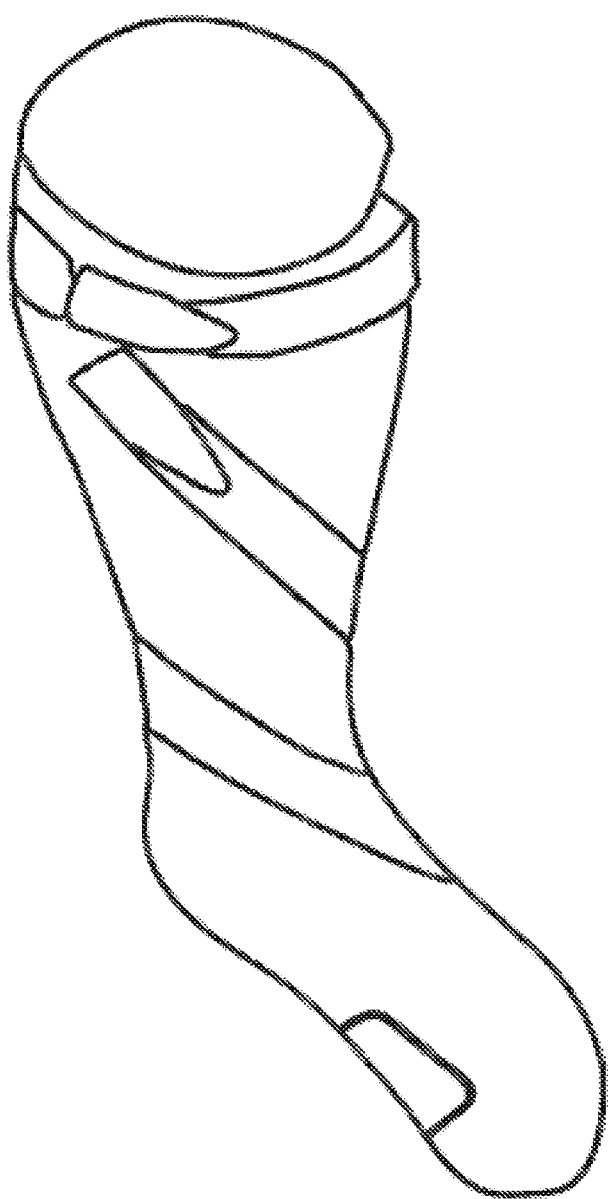
FIG. 1A is a perspective view of another implementation similar to those variants shown in FIG. 1, in accordance with the principles of the present disclosure.

FIG. 1A illustrates another variant of orthoses 100, 150, which uses a Velcro system to anchor the suspension strap at the top of the calf as well as for the adjustable rotation/dorsi flexion support strap. In this configuration, both straps may be stretchable or may be inelastic. In implementations in which one or more of these straps is stretchable, these straps may provide for dynamic (e.g., changing) support throughout the entire gait cycle. The sock properties may remain the same (or similar) as those described with respect to orthoses 100, 150. Each strap may be permanently attached to sock via, for example, a sewed end at one end and attached through a "D ring" at another end. In some implementations, the D rings may be soft and pliable and could also be sewn into the sock as well in some implementations.

Figure 2:
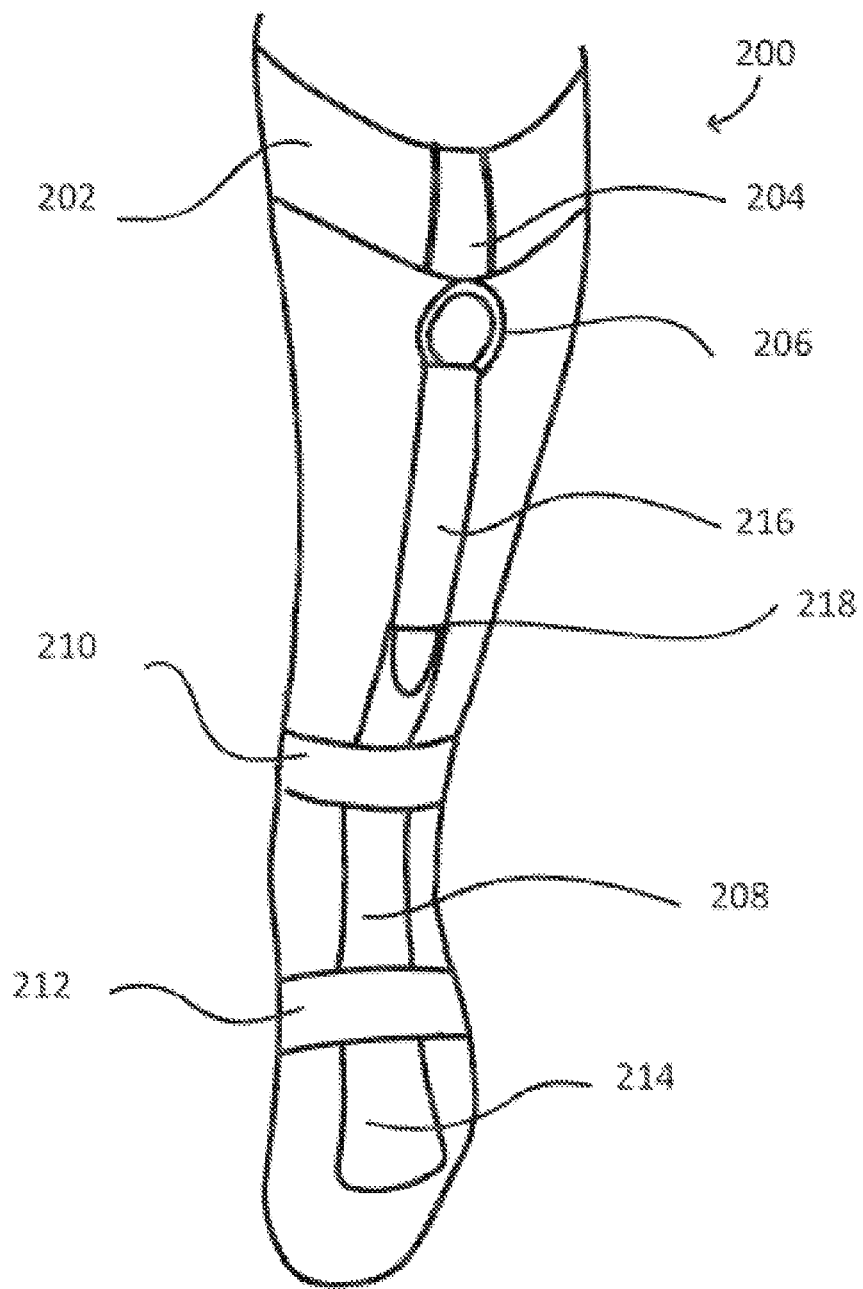
FIG. 2 is a front perspective view of another exemplary orthoses device that has been integrated into a sock, in accordance with the principles of the present disclosure.

Referring now to FIG. 2, another foot ankle orthoses 200 is shown and described in detail. Orthoses 200 has been integrated into a sock. In some implementations, the sock has minimal if any vertical stretch going from the toes up the calf so as to maintain, for example, an appropriate amount of tension (e.g., by pulling the ankle into dorsiflexion) thereby reducing the effects associated with the drop foot condition, while allowing for an increased amount of stretch in the horizontal direction so as to, inter alia, make it easy to put on and/or take off the orthoses 200.

Similar to the embodiments illustrated in FIG. 1, the orthoses 200 includes an adjustable strap 202 positioned, for example, above the calf muscle. Adjustable strap 202 further includes a support structure 204 having support ring 206. In some implementations, support structure 204 may be sewn or otherwise fixedly attached to adjustable strap 202. In alternative implementations, support structure 204 may be removably attached to, for example, adjustable strap 202 such as via, for example, Velcro, or a clip (e.g., that is positioned over the top of adjustable strap 202, or mates with a respective hook or other means on (or underneath) the adjustable strap 202, etc.).

Orthoses 200 may further include an ankle strap 210 and a foot strap 212. Ankle strap 210 and foot strap 212 assists in keeping the support strap 208 flush against the leg when under tension. While the support strap 208 is depicted as running underneath the ankle strap 210 and foot strap 212, it would be readily appreciated by one of ordinary skill given the contents of the present disclosure that alternative configurations are readily appreciated. For example, one or both of ankle strap 210 and foot strap 212 may include, for example, a low friction interface that may run through the middle of ankle strap 210 and/or foot strap 212 or may be placed on the top surface of the ankle strap 210 and/or foot strap 212. One or both of ankle strap 210 and foot strap 212 may be fixedly secured to the sock, or alternatively may be removably secured (e.g., strap 210 and/or strap 212 may be separately attachable) in order to allow, for example, further customization of the positioning of these straps 210, 212 in relation to a given user's anatomy.

Support strap 208 may be fixedly secured adjacent to the toe region of the sock. The opposite end 216 of the support strap 208 may be routed through support ring 206 and secured back on itself in order to bring the foot into, for example, a neutral to slight dorsiflexion thereby limiting plantarflexion of the ankle which may be advantageous in addressing, for example, the aforementioned drop foot condition. In some implementations, an identifiable marker 218 may be placed on the support strap 208 so as to enable a user of the orthoses to apply an appropriate level of tension for their desired level of, for example, their drop foot condition. In some implementations, the identifiable marker 218 may be obviated in view of another mechanism (e.g., Velcro, clasp, or other mechanism) in order to ensure a repeatable amount of an appropriate level of tension for a given user. In some implementations, the level of tension may be determined by a doctor or other skilled technician as opposed to being determined by the user themselves.

Referring now to FIGS. 3A-3D, various different configurations of strapping that may be utilized in order to provide a combination of dorsiflexion/inversion/eversion/rotation support is shown and described in detail. While the orthoses 300 shown in FIGS. 3A-3D is shown as being used as a separate device, it would be readily appreciated by one of ordinary skill given the contents of the present disclosure that the orthoses of FIGS. 3A-3D may be integrated into a sock (such as a sock similar to that illustrated in FIG. 2) in some implementations.

Figure 3A:
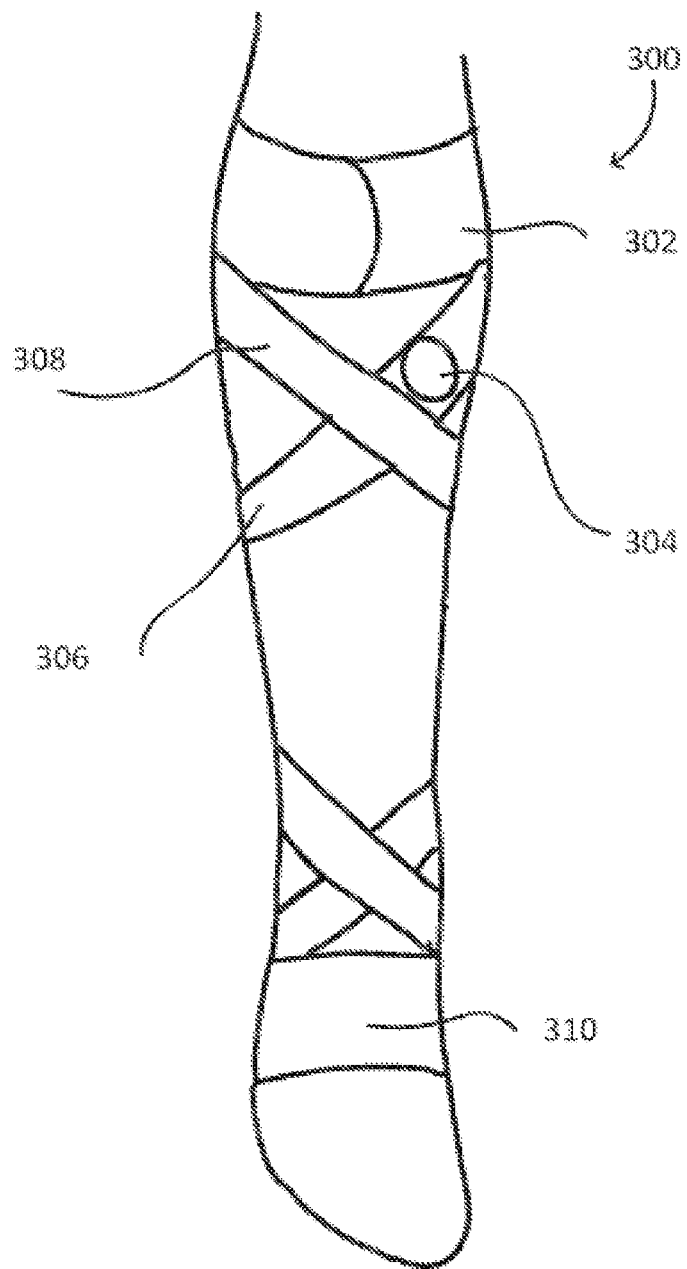
FIG. 3A is a front perspective view of yet another exemplary orthoses, in accordance with the principles of the present disclosure.

FIG. 3A illustrates an orthoses 300 with an adjustable strap 302 (e.g., a Velcro strap) that is disposed at, for example, the top of the calf muscle. Similar to other implementations described elsewhere herein, the disposition of the adjustable strap at the top of the calf muscle may be advantageous in some implementations as securing the strap 302 may prevent the top of the orthoses from being pulled down over the calf muscle when the support strap 306, 308 is tightened. Support strap 306 may include a rotary tensioning dial 304 (e.g., a BOA® tensioning system) that is configured to provide tension to the support straps 306, 308. Orthoses 300 may further include a supporting structure 310 (and sock in some implementations) that may allow for circumferential stretching as a means by which orthoses 300 remains comfortable to wear by a user. In the illustrated embodiment, supporting structure provides for an anchor point for straps 306, 308 around the dorsum of the foot in the metatarsal region. Supporting structure 310 may possess a more limited ability to stretch in the longitudinal direction (e.g., along the dorsum of the foot) in order to maintain, for example, an appropriate amount of tension (e.g., by pulling the ankle into dorsiflexion) when support straps 306, 308 are placed under tension, thereby reducing the effects associated with the drop foot condition.

The adjustable strap 302 may also possess two anchor points, one for attachment of strap 306 (via rotary tensioning system 304) and one for attachment of strap 308. In some implementations (such as that illustrated in FIG. 3A), strap 306 is configured to be anchored medially on adjustable strap 302, while strap 308 is configured to be anchored laterally on adjustable strap 302. In some implementations (not shown), the positioning of these anchor points may be reversed such that strap 308 is anchored medially on adjustable strap 302, while strap 306 may be anchored laterally on adjustable strap 302. The two adjustable straps 306, 308 may be made from an elastic material in some implementations and are configured to connect to each respective anchor point on the adjustable strap 302 such that they spiral around the leg in opposite directions from one another. In other words, as illustrated strap 306 may be wound around the leg of a user in a clockwise direction, while strap 308 may be wound around the leg of a user in a counter-clockwise direction. The orthoses 300 illustrated in FIG. 3A is configured to provide a dynamic dorsi-flexion support with inversion/eversion support as well as provide for rotational stability for the ankle. In some implementations, each of straps 306, 308 may be discrete components (i.e., separate components) that may either be fixedly secured or, alternatively, may be removably secured to supporting structure 310. In alternative implementations, each of straps 306, 308 and supporting structure 310 may be manufactured as a unitary component.

Figure 3B:
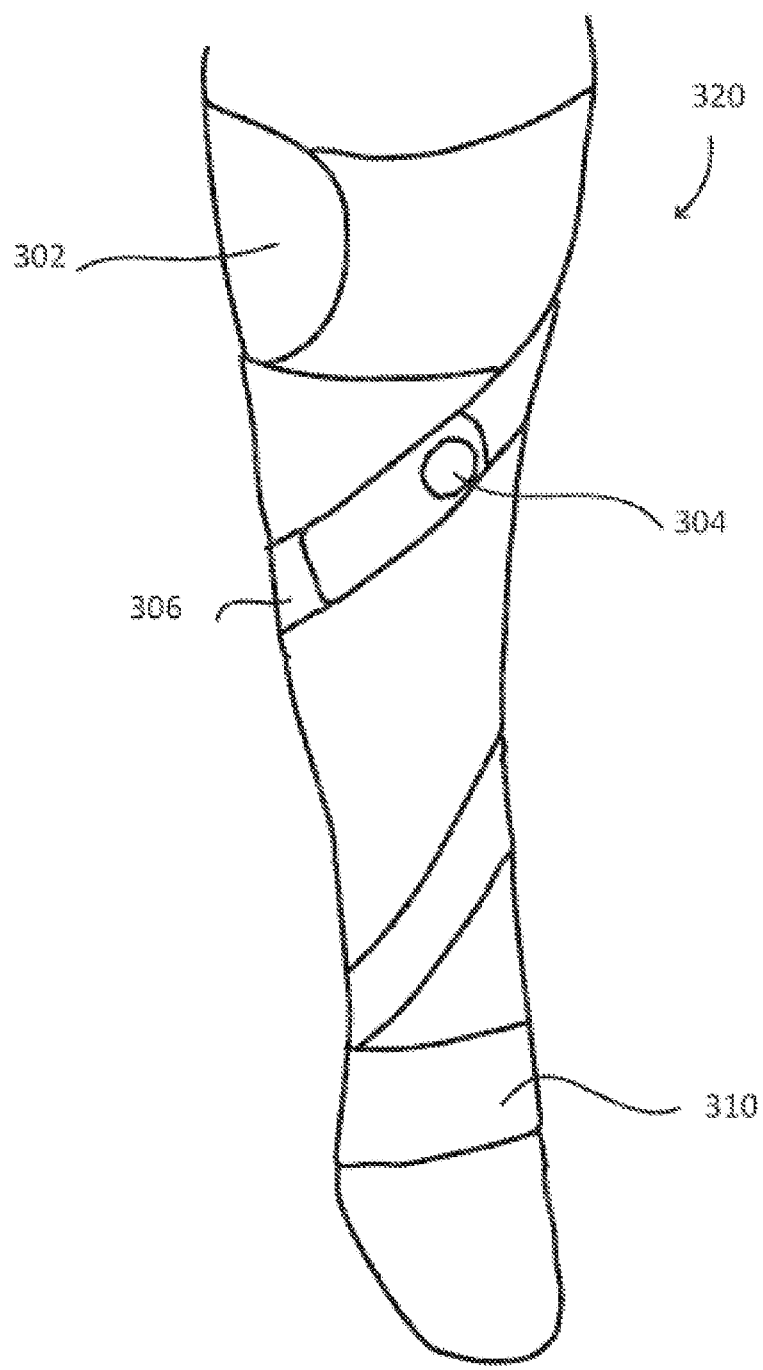
FIG. 3B is a front perspective view of the orthoses depicted in FIG. 3A that is being utilized in a first configuration, in accordance with the principles of the present disclosure.

Referring now to FIG. 3B, an alternative configuration 320 to that shown in FIG. 3A is shown. In this particular configuration, strap 306 may be medially attached to the adjustable strap 302 and laterally attached to the supporting structure 310. In such a configuration, orthoses 320 may create a dynamic dorsi-flexion support with inversion support as well as providing for rotational stability for the ankle.

Figure 3C:
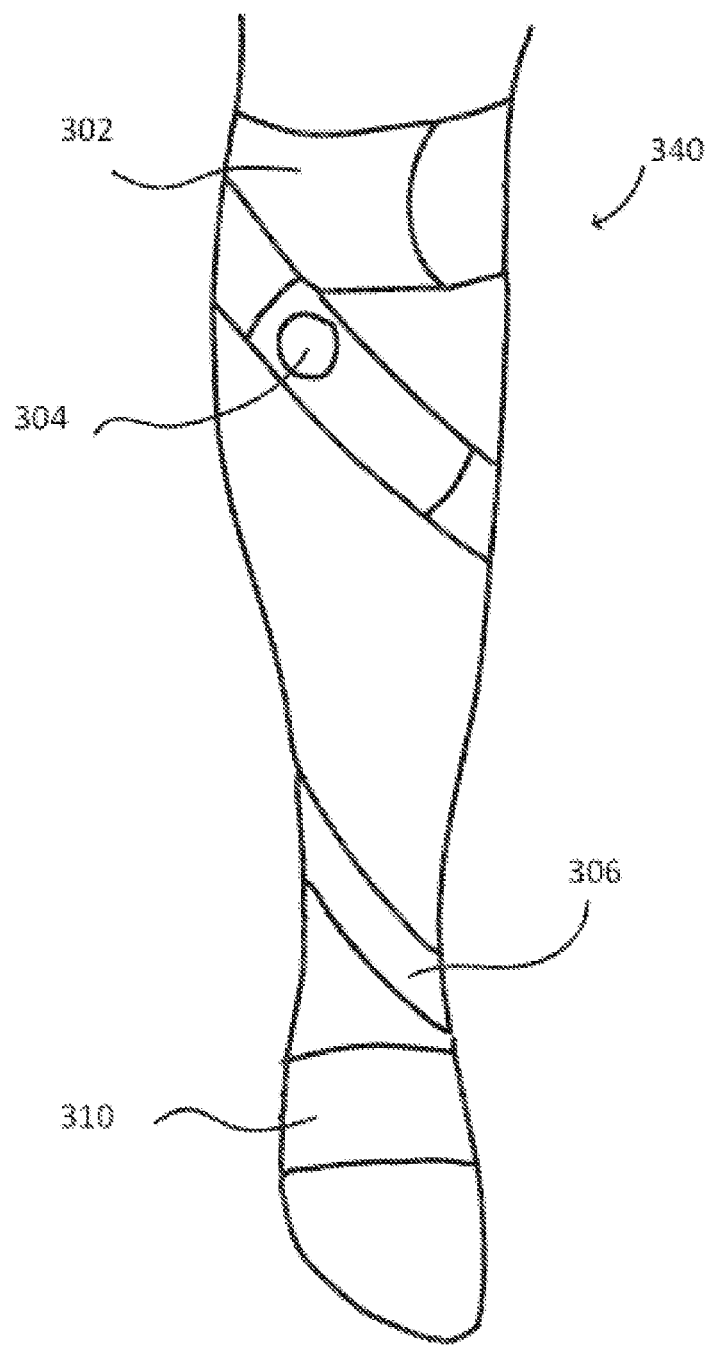
FIG. 3C is a front perspective view of the orthoses depicted in FIG. 3A that is being utilized in a second configuration, in accordance with the principles of the present disclosure.

Referring now to FIG. 3C, yet another alternative configuration 340 to that shown in FIGS. 3A and 3B is shown and described in detail. In this particular configuration, strap 306 may be laterally attached to the adjustable strap 302 and medially attached to the supporting structure 310. In such a configuration, orthoses 340 may create a dynamic dorsiflexion support with eversion support as well as providing for rotational stability for the ankle.

In some implementations, the support strap may be secured, for example, medially (or laterally) at the top of the calf of a user at a top anchor point. The support strap may then spiral across the knee joint and ultimately be positioned on the same side as the top anchor point on the foot. Such a configuration may possess advantages in providing dynamic knee support for, for example, Osteoarthritis treatment.

Referring now to FIGS. 4A-4F, yet another ankle foot orthoses 400 is shown and described in detail. In particular, orthoses 400 is manufactured as a sock. In some implementations, the sock is manufactured so as to have a high stretch in the horizontal direction (e.g., across the foot, etc.), and a lesser amount of stretch in the vertical direction (e.g., along the shin). As discussed elsewhere herein, this high stretch in the horizontal direction enables the orthoses 400 to be taken on (and off easily), while the low stretch in the vertical direction assists in providing the requisite support to enable sufficient dorsi-flexion support for the foot. An adjustable strap 402 is provided for positioning and retention of the orthoses at, for example, the top of the calf of a user. The adjustable strap 402 may be adjusted using, for example, Velcro in some implementations. Other securing means may be provided in addition to, or alternatively from the aforementioned Velcro, in other implementations including, without limitation, fasteners such as buttons, clasps, snaps/press studs, zippers, safety pins, hooks and eye fasteners, frog fasteners, toggle fasteners, metal fasteners, grommets/eyelets, glass studs, and the like. Adjustable strap 402 further includes a support structure 404 having an attachment point 406. In some implementations, support structure 404 may be sewn or otherwise fixedly attached to adjustable strap 402. In alternative implementations, support structure 404 may be removably attached to adjustable strap 402 such as via, for example, Velcro, a clip (e.g., that is positioned over the top of adjustable strap 402, or mates with a respective hook or other means on (or underneath) the adjustable strap 402, etc.).

Orthoses 400 may further include an ankle strap 410 and a foot support 414 which provides for additional adjustable anchor points in the ankle region and around the toe area of the foot in some implementations. Ankle strap 410 (and to an extent foot support 414) assists in keeping the support strap 408 flush against the leg/foot when under tension. This ability to keep the support strap 408 flush against the leg/foot enables the orthoses 400 to be utilized with, for example, shoes. The support strap 408 provides for an adjustable tensioning mechanism that is configured to connect to a connecting point 412, travel over the dorsum of the foot through (or underneath) ankle strap 410, and up the tibia for attachment to attachment point 406 located on the support structure 404. In some implementations, support strap may include one or more of a tensioning cable, an inelastic strap, or an elastic strap. Accordingly, by appropriately tensioning support strap 408, one may provide for sufficient dorsi-flexion support. While the support strap 408 is depicted as running underneath the ankle strap 410, it would be readily appreciated by one of ordinary skill given the contents of the present disclosure that alternative configurations are readily appreciated. For example, the ankle strap 410 may include, for example, a low friction interface that may run through the middle of ankle strap 410 or may be placed on the top surface of the ankle strap 410. Ankle strap 410 may be fixedly secured to the sock, or alternatively may be removably secured (e.g., strap 410 may be separately attachable) in order to allow for, for example, further customization of the positioning of this strap 410 in relation to a given user's anatomy.

Support strap 408 may be fixedly secured adjacent to the foot support 414 of the sock. The opposite end of the support strap 408 may be secured at or near support ring 406 in order to bring the foot into, for example, a neutral to slight dorsiflexion thereby limiting plantarflexion of the ankle which may be advantageous in addressing, for example, the aforementioned drop foot condition. For example, in some implementations (such as that shown in FIG. 4A), foot support 414 may be positioned over the user's toes and may include a closed sleeve (or pocket) at connecting point 412. In some implementations, foot support 414 may be placed on the medial side (and/or lateral side) of the foot (e.g., adjacent to the metatarsal region). Such a configuration may be useful in providing additional eversion (and/or inversion) support, particularly when support strap 408 (or support straps) are wrapped around the lower portion of the user's leg (such as in the fashion described with respect to the implementations of FIGS. 3A-3C). Moreover, in some implementations, the support ring 406 may be obviated in view of a rotary tensioning mechanism such as that described with respect to, for example, FIGS. 3A-3C.

Figure 4A:
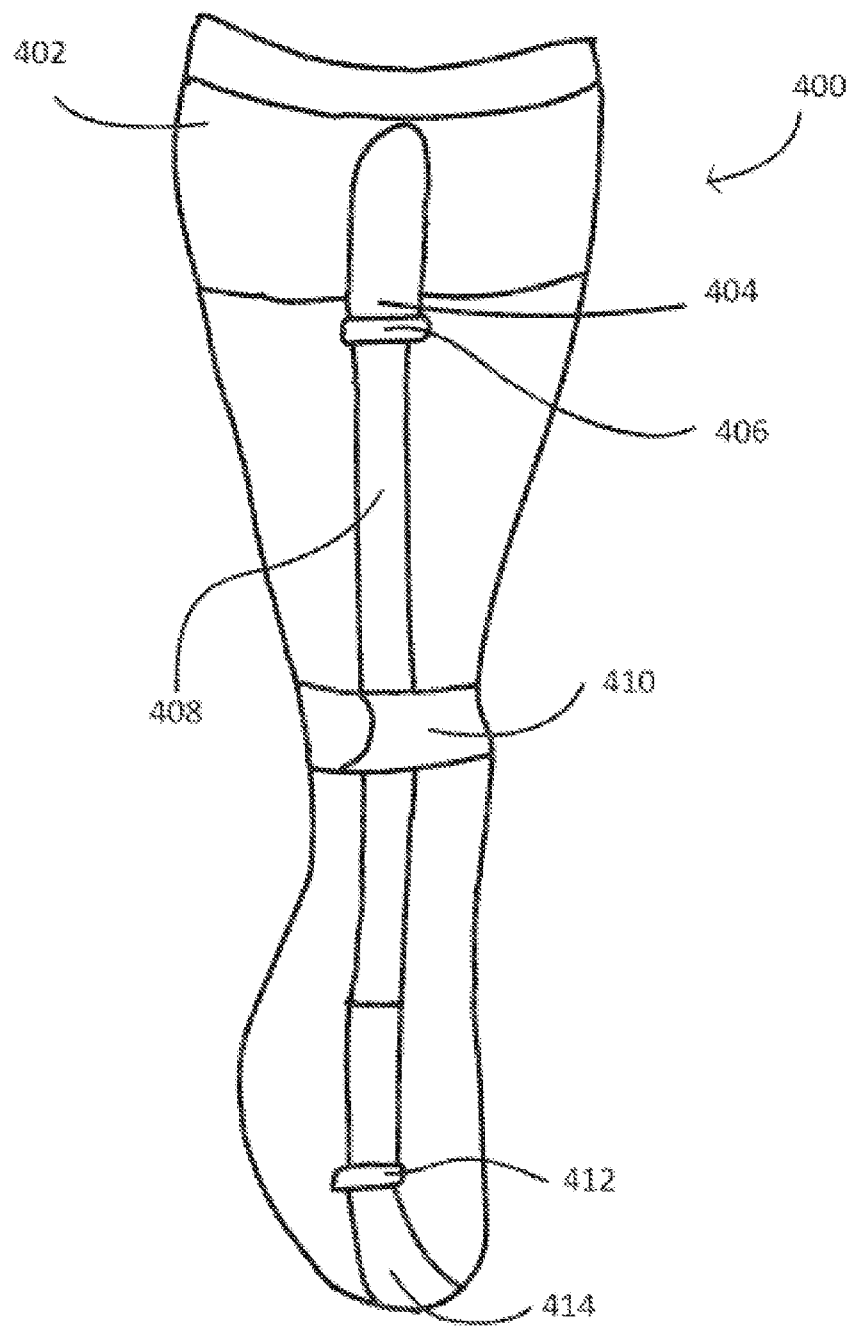
FIG. 4A is a front perspective view of yet another exemplary orthoses device that been integrated into a sock, in accordance with the principles of the present disclosure.
Figure 4B:
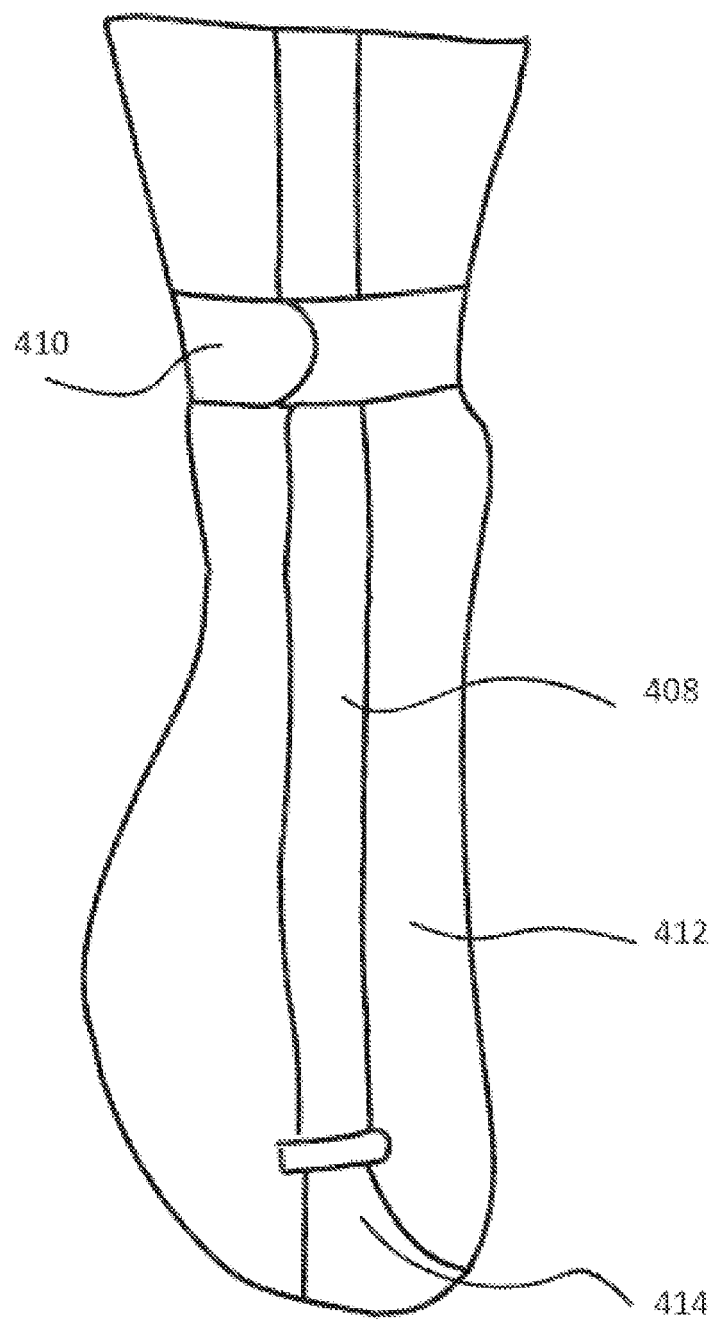
FIG. 4B is a front perspective view of the toe region of the exemplary orthoses device depicted in FIG. 4A, in accordance with the principles of the present disclosure.

FIG. 4B illustrates a close up view of the foot region of orthoses 400. In particular, support cables 408 are shown adjacent to connecting point 412. In particular, connecting point 412 includes a sleeve through which support cables 408 may be routed therethrough.

Figure 4C:
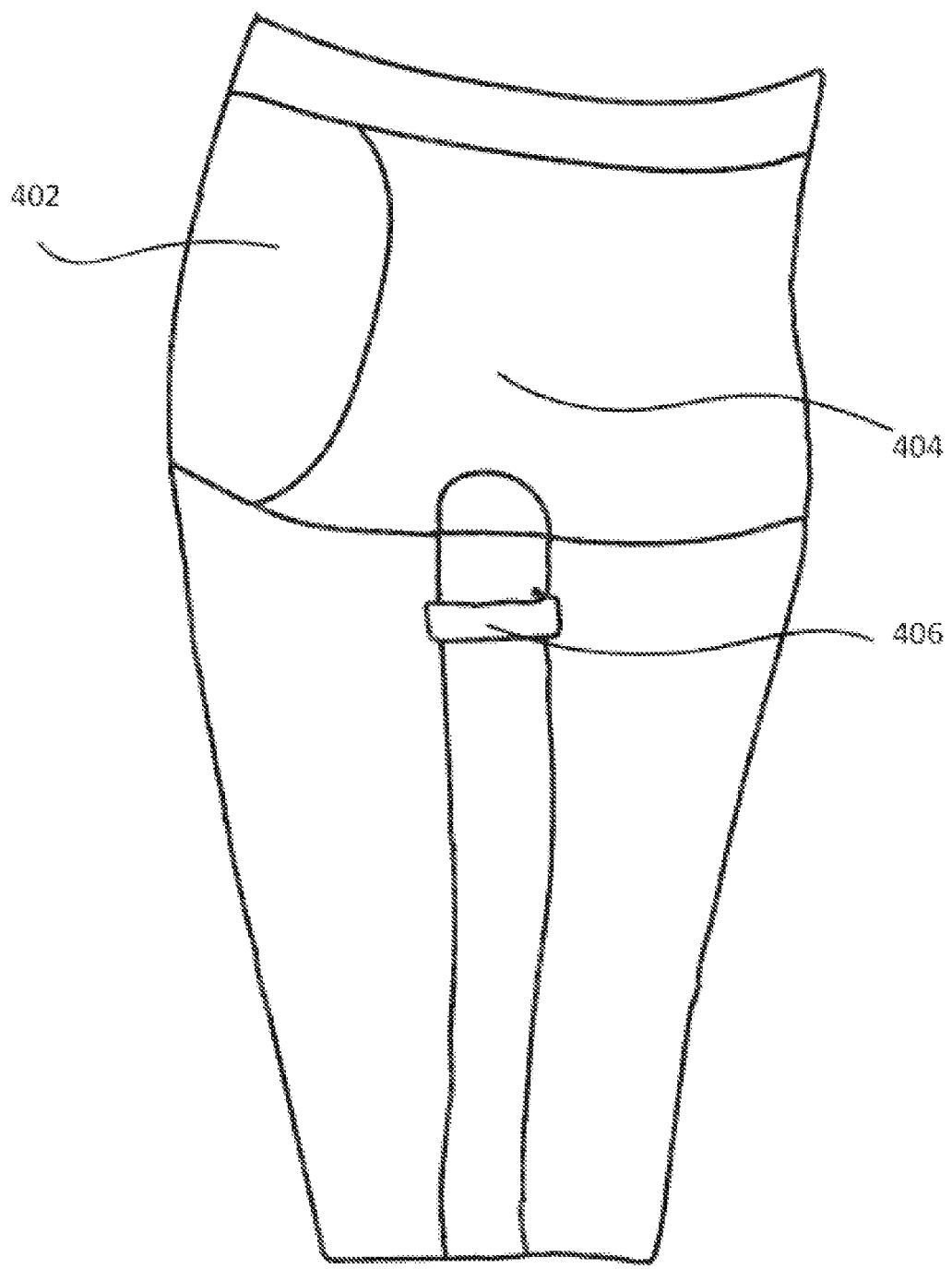
FIG. 4C is a front perspective view of the top region of the exemplary orthoses device depicted in FIG. 4A, in accordance with the principles of the present disclosure.

FIG. 4C illustrates the top portion of orthoses 400. In particular, in some implementations, support structure 404 may be removably attached to the upper portion of orthoses via Velcro. In some implementations, the length dimension of support structure 404 may, in combination with the length of support straps/cables 408 be configured to provide a predetermined amount of tension when placed at top portion of orthoses so as to ensure, inter alia, an appropriate amount of dorsi flexion. In some implementations, other attachment methods may be utilized including one or more of a buckle, a magnet, and/or other fastening methods. In yet other implementations, support structure may be non-adjustable, while still promoting sufficient dorsi flexion support.

Figure 4D:
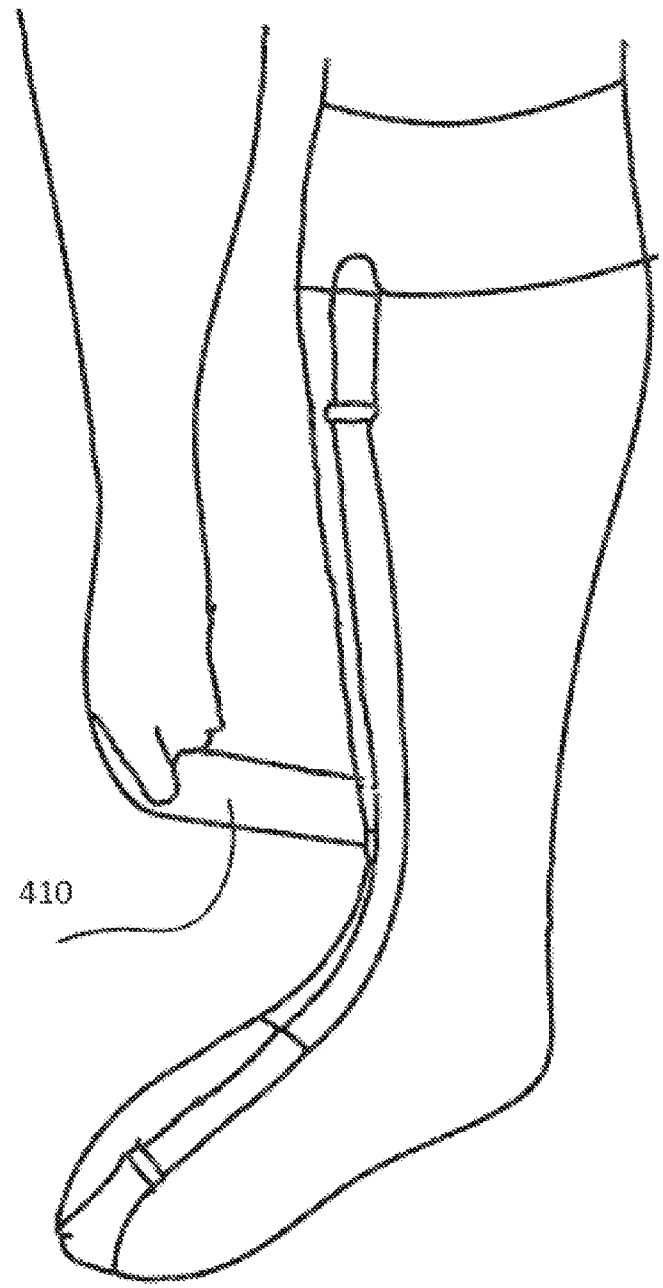
FIG. 4D depicts the adjustment of the ankle strap of the exemplary orthoses device depicted in FIG. 4A.
Figure 4E:
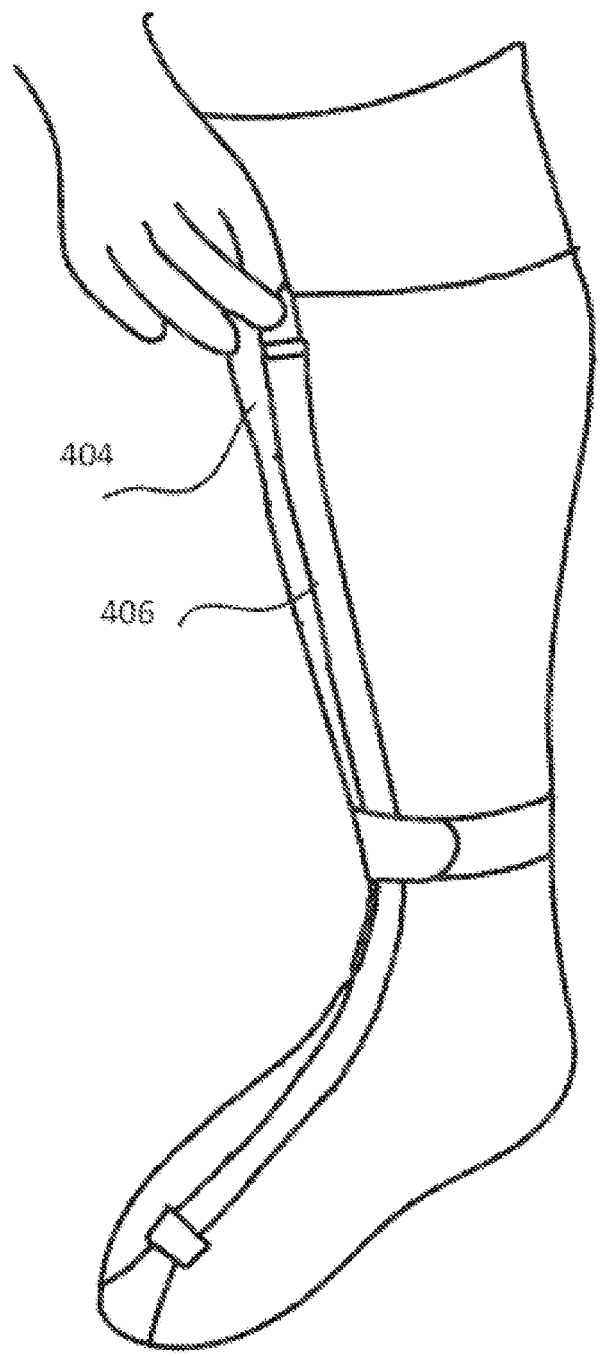
FIG. 4E depicts the adjustment of the support structure and the attachment point of the exemplary orthoses device depicted in FIG. 4A.
Figure 4F:
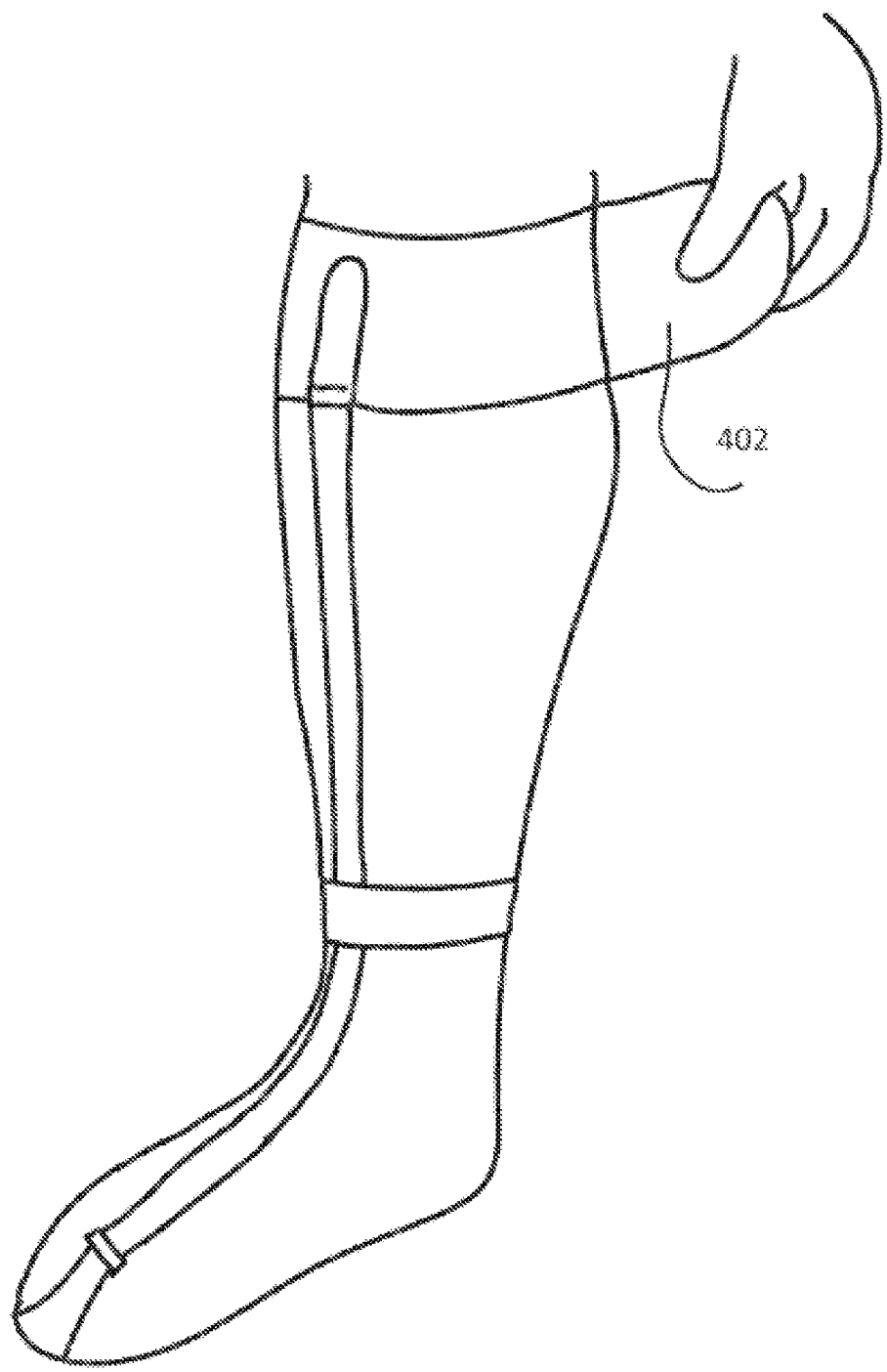
FIG. 4F depicts the adjustment of the adjustable strap of the exemplary orthoses device depicted in FIG. 4A.

FIG. 4D illustrates the adjustment of ankle strap 410 with Velcro. In particular, ankle strap 410 ensures that the support strap 408 (e.g., dorsi flexion assist strap) is maintained close to the leg at all times when support strap 408 is placed under tension. FIG. 4E illustrates the adjustment of support structure 404 and attachment point 406 which enables, inter alia, that the support strap 408 (e.g., dorsi flexion assist strap) can be adjusted in terms of tension. FIG. 4F illustrates adjustment of the adjustable strap 402 in accordance with some implementations of the present disclosure. The use of adjustable strap 402 ensures that the sock doesn't slip down the leg when the support strap 408 is tightened.

Figure 5A:
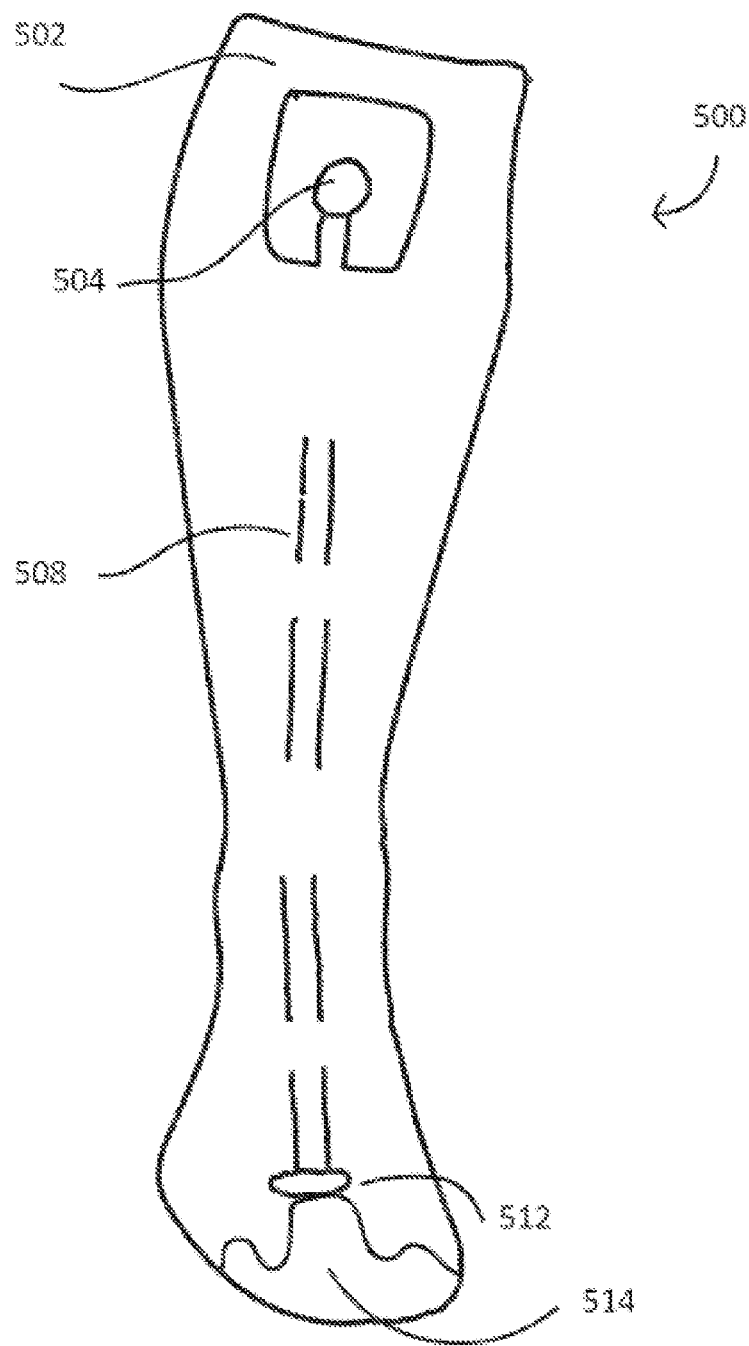
FIG. 5A is a front perspective view of yet another exemplary orthoses device that been integrated into a sock, in accordance with the principles of the present disclosure.
Figure 5B:
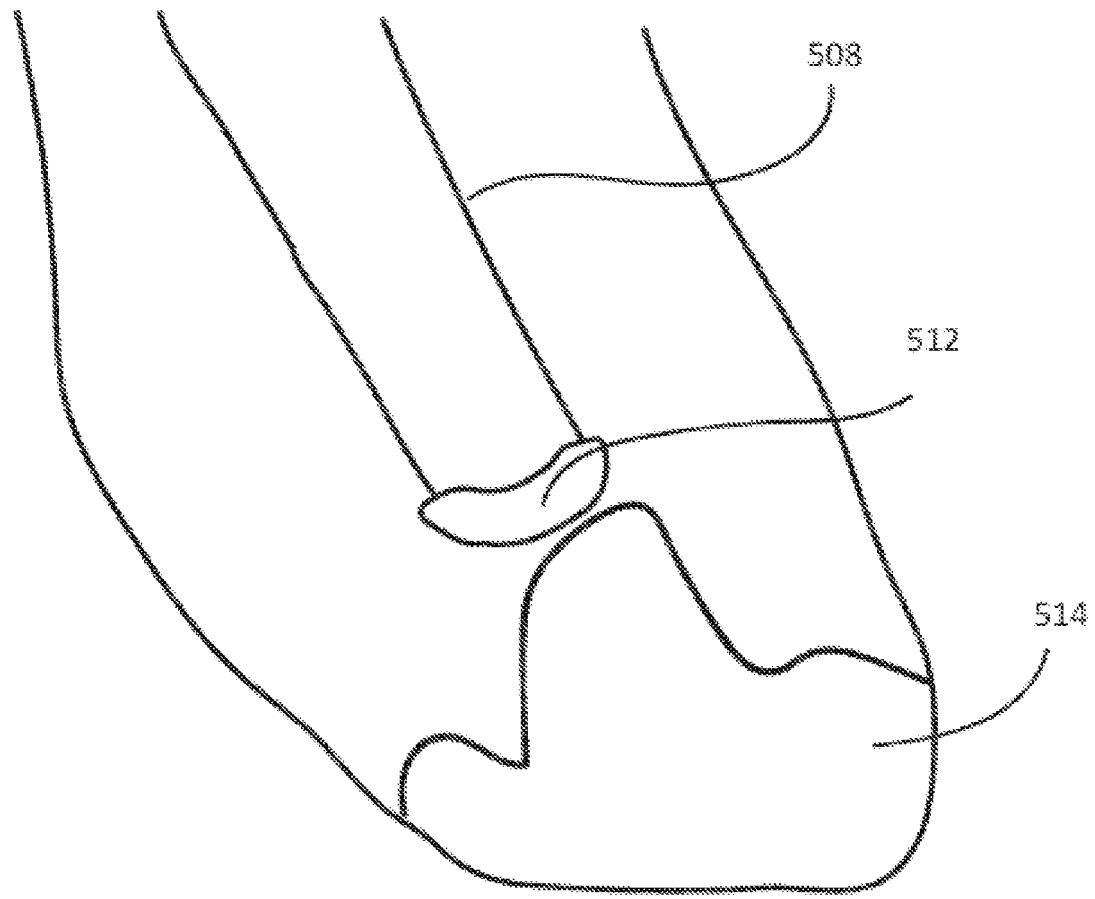
FIG. 5B is a front perspective view of the toe region of the exemplary orthoses device depicted in FIG. 5A, in accordance with the principles of the present disclosure.
Figure 5C:
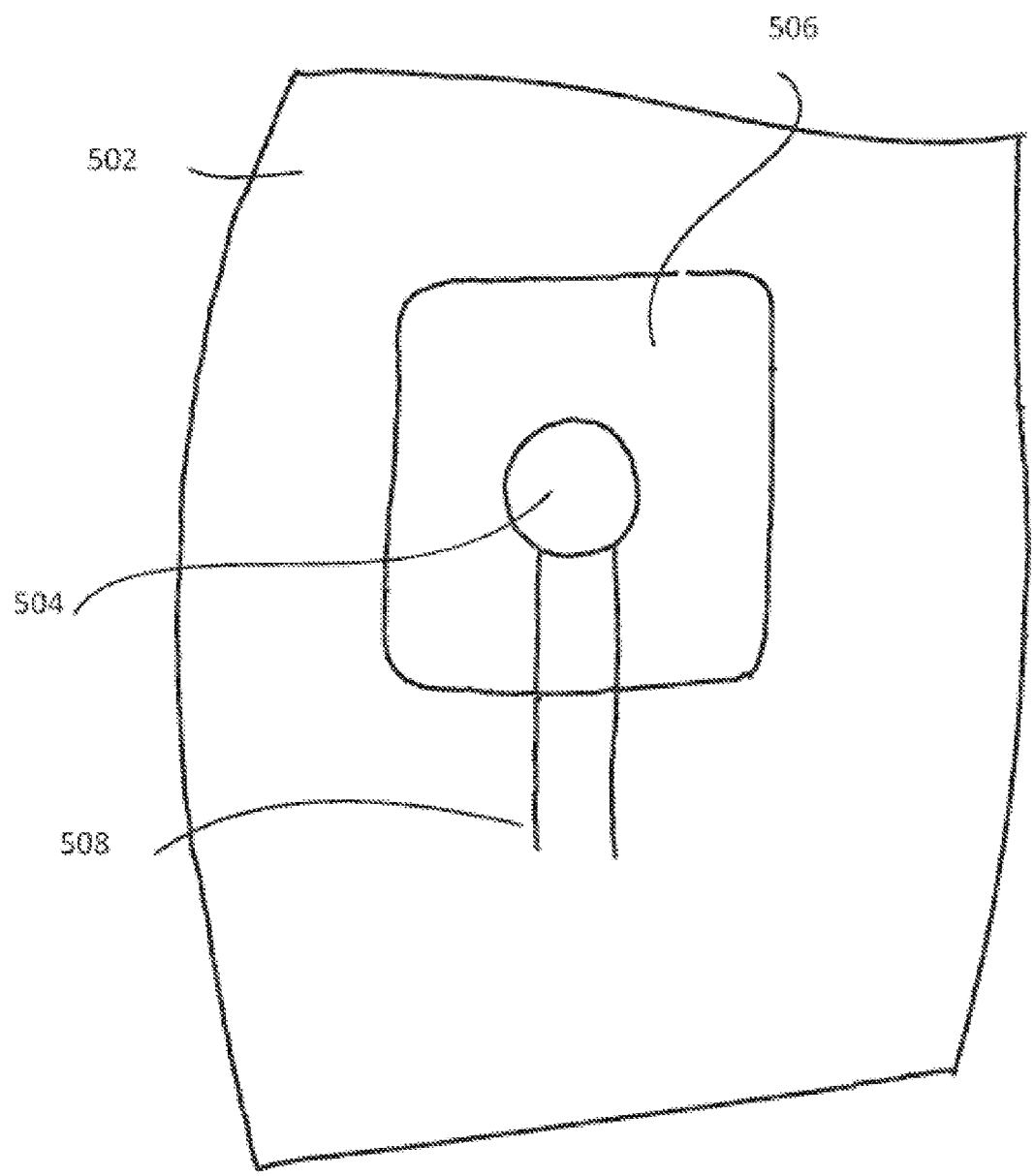
FIG. 5C is a front perspective view of the top region of the exemplary orthoses device depicted in FIG. 5A, in accordance with the principles of the present disclosure.

Referring now to FIGS. 5A-5C, yet another foot ankle orthoses 500 is shown and described in detail. In particular, orthoses 500 has been integrated into a sock. In some implementations, orthoses 500 includes a retention structure 502, a support structure for a rotatory tensioning mechanism 504, support strap(s) (or cable(s)) 508, attachment point 512, and supporting structure 514 disposed adjacent to the toes of a user of orthoses 500. The underlying drop foot sock may, in some implementations, include low stretch in the horizontal direction in the region of the ankle and at the top of the calf (i.e., in the region of retention structure 502). The underlying drop foot sock may include a higher amount of stretch in the horizontal direction in one or more other regions so as to enable orthoses 500 to be put on, and taken off, easily, while also providing for improved comfort. Orthoses 500 may also include low stretch in the vertical direction to ensure proper stability of the dorsi flexion support strap/cable 508.

Moreover, in the illustrated embodiment, support strap 508 is shown as an inelastic cable that is threaded within the underlying sock so as to enable, inter alia, the obviation of an ankle support strap. In some implementations, the inelastic cables are threaded in and out of the sock twice along the tibia region, and threaded in again just above the ankle and out again adjacent the navicular bone of the foot. In some implementations, the support strap 508 (e.g., inelastic cable) may be threaded into the underside of sock (i.e., support strap 508 may be threaded so that portions thereof are disposed adjacent to, for example, the skin of a wearer of orthoses 500), while in other implementations the support strap 508 may be threaded inside of the sock such that the material of the sock is disposed between the skin of a wearer and the support strap 508 so as to mitigate irritation to the user's skin by support strap 508 in some implementations. In some implementations, it may be desirable to thread support strap 508 entirely within the sock. Regardless of the particular implementation chosen, by virtue of the support strap 508 being threaded into (and out of) the underlying sock material (or within the underlying sock material), the support strap 508 may be placed proximate to the user's foot/leg when the support strap 508 is placed under tension via, for example, rotary tensioning mechanism 504. In other implementations (not shown), the support strap may be disposed entirely (or almost entirely) within the sock (or underneath the sock) for the purpose of making orthoses 500 aesthetically pleasing. Preferably, orthoses 500 may be utilized with (or without) a standard set of shoes, boots, etc.

Referring now to FIG. 5B, a close up view of the toe region of orthoses 500 is shown and described in detail. In particular, connecting point 512 is shown which may comprise a plastic material having a curved routing cavity for receiving support strap 508. Additionally, in some implementations, a supporting structure 514 may be disposed adjacent to connecting point 512, The purpose of supporting structure 514 is to, inter alia, prevent the vertical stretch of orthoses 500 in this particular region when support strap 508 is placed under tension. In some implementations, both supporting structure 514 and connecting point 512 are attached to the underlying sock by being threaded thereon.

Referring now to FIG. 5C, a close up view of the top portion of orthoses 500 is shown and described in detail. Specifically, unlike prior embodiments, the top portion of orthoses does not include an adjustable strap in the illustrated embodiment. Rather, the retention structure 502 may be formed from the underlying sock material that enables orthoses 500 to remain secured above a user's calf muscle without having to apply an additional tightening step (such as that shown with reference to FIG. 4F). In other words, retention structure 502 ensures that a sufficient amount of horizontal tension of the underlying sock material is placed around the top of a user's calf muscle so as to enable the sock to stay in place when support strap 508 is tightened. Additionally, rotary tensioning dial 504 may be attached to a supporting fabric 506 which is sewn in the top region of orthoses 500. Accordingly, through use of supporting fabric 506, retention structure 502 and supporting structure 514 (FIG. 5B), additional support may be provided to orthoses 500 so as to prevent the top of orthoses 500 from being pulled down over, for example, a user's calf muscle when support strap 508 is placed under tension.

Figure 6A:
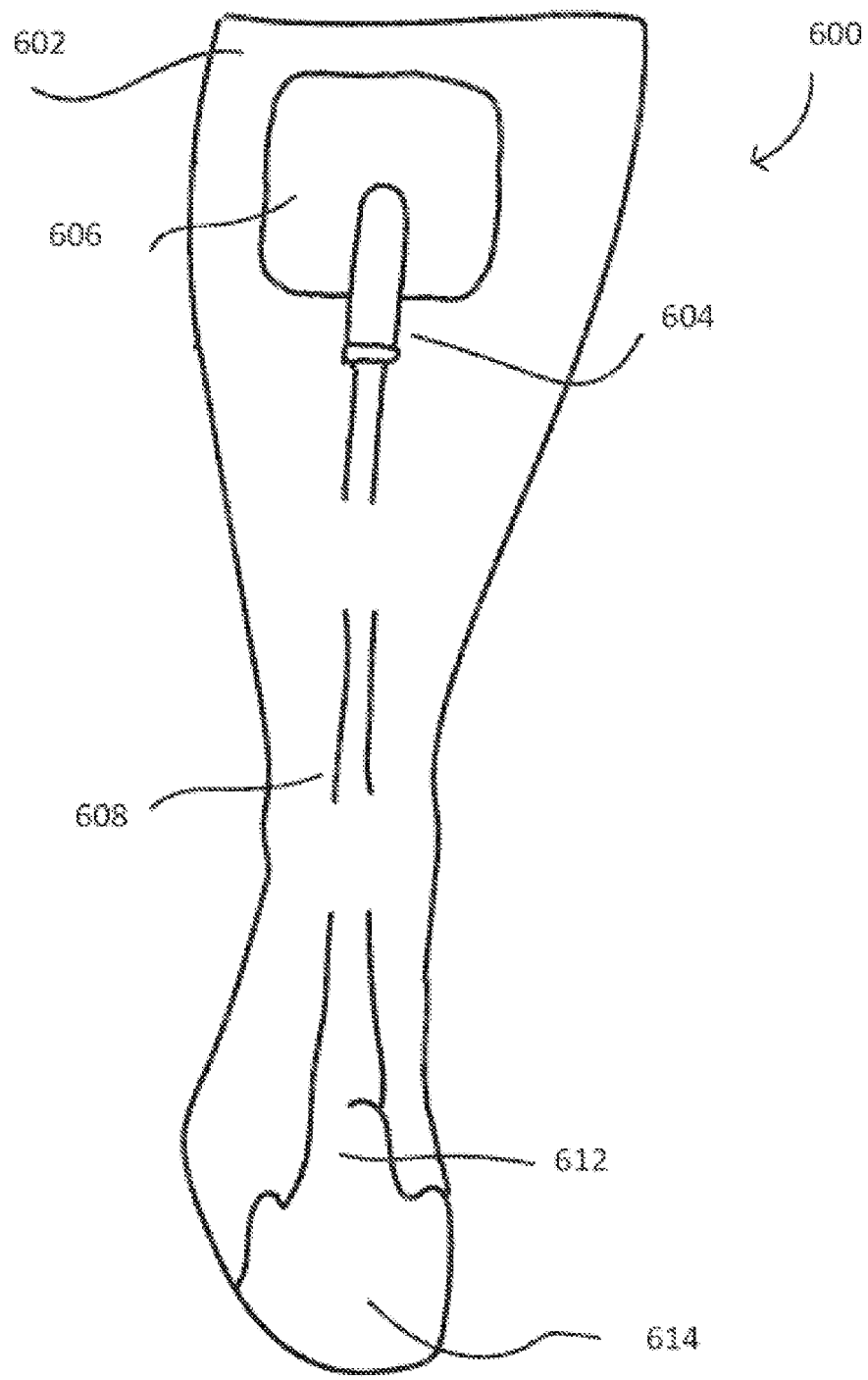
FIG. 6A is a front perspective view of yet another exemplary orthoses device that been integrated into a sock, in accordance with the principles of the present disclosure.
Figure 6B:
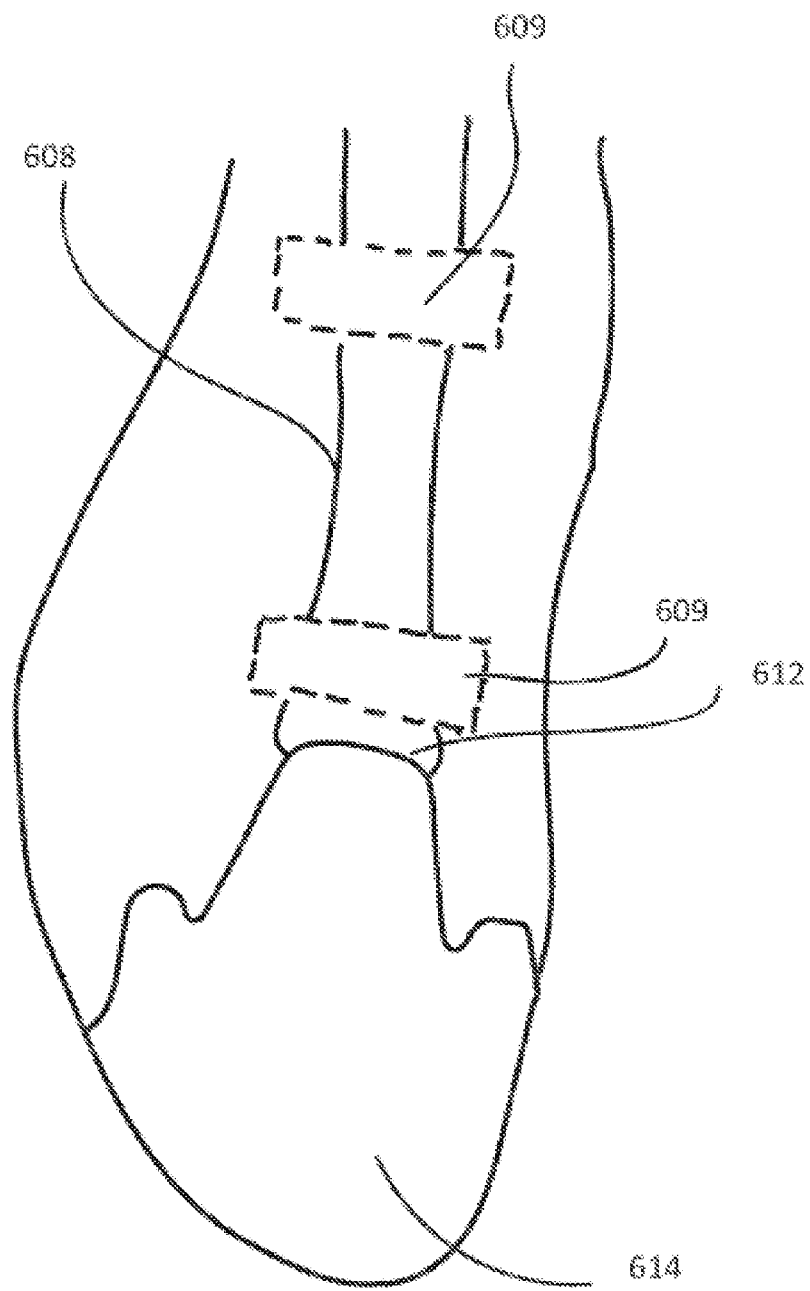
FIG. 6B is a front perspective view of the toe region of the exemplary orthoses device depicted in FIG. 6A, in accordance with the principles of the present disclosure.
Figure 6C:
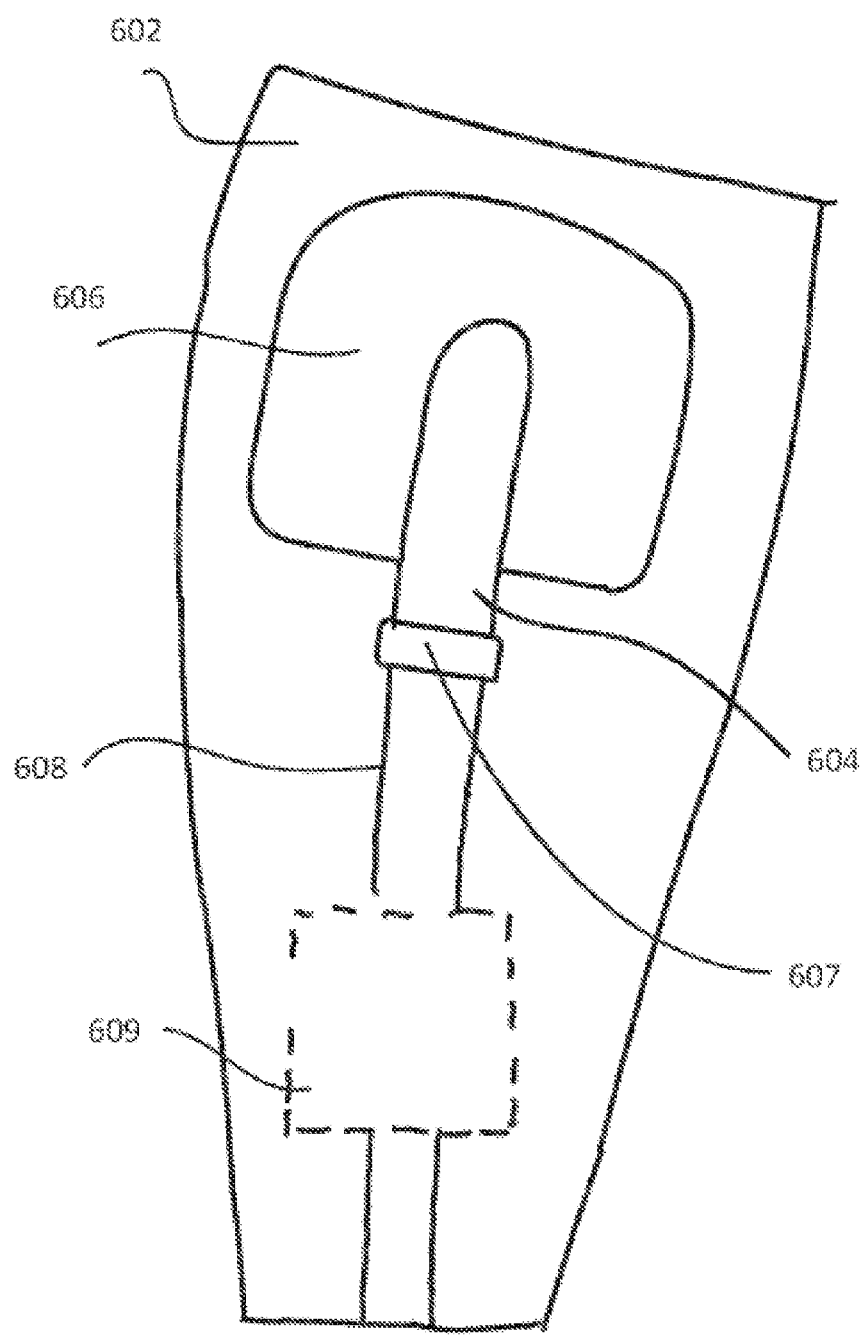
FIG. 6C is a front perspective view of the top region of the exemplary orthoses device depicted in FIG. 6A, in accordance with the principles of the present disclosure.

Referring now to FIGS. 6A-6C, a similar orthoses 600 is shown as that shown and described with respect to FIGS. 5A-5C. In particular, orthoses 600 has been integrated into a sock, and further orthoses 600 includes a tensioning strap 602, support strap(s) or cable(s) 608, attachment point 612, and a supporting structure 614 disposed adjacent to the toes of a user of orthoses 600. The underlying drop foot sock may, in some implementations, include low stretch in the horizontal direction in the region of the ankle and at the top of the calf. The underlying drop foot sock may further include a higher amount of stretch in the horizontal direction in other portions of orthoses 600 so as to enable orthoses 600 to be put on, and taken off, relatively easily, while also providing for improved comfort. Orthoses 600 may also include low stretch in the vertical direction to ensure proper stability of the dorsi flexion support strap/cable 608. However, unlike like orthoses 500 shown with respect to FIGS. 5A-5C, orthoses 600 includes, for example, a Velcro structure 604 that is utilized to apply tension to support straps 608 as will be described subsequently herein with respect to FIG. 6C.

FIG. 6B illustrates the toe region of orthoses 600. In particular, connecting point 612 is shown which may comprise a fabric that includes a channel through which support strap 608 is received. By virtue of being made from fabric, connecting point 612 may provide for added comfort when orthoses 600 is worn with, for example, shoes. In some implementations, connecting point 612 may instead include a plastic material having a curved routing cavity for receiving support strap 608 (similar to that described with reference to FIG. 5B). Additionally, in some implementations, a supporting structure 614 may be disposed adjacent to connecting point 612, The purpose of supporting structure 614 is to, inter alia, prevent the vertical stretch of orthoses 600 in this particular region when support strap 608 is placed under tension. In some implementations, both supporting structure 614 and connecting point 612 are attached to the underlying sock by being threaded thereon. Additionally, regions 609 where support strap 608 may be woven within (or underneath) the underlying sock material is also illustrated.

Referring now to FIG. 6C, a close up view of the top portion of orthoses 600 is shown and described in detail. Specifically, and similar to that described with reference to FIG. 5C, the top portion of orthoses 600 does not include an adjustable strap in the illustrated embodiment. Rather, the tensioning strap 602 may include a reinforced structure that enables orthoses 600 to remain secured above a user's calf muscle without having to apply an additional tightening step (such as that shown with reference to FIG. 4F). Additionally, the Velcro structure 604 may be more readily seen. In particular, Velcro structure 604 may be secured to a Velcro portion of material 606 at a top region of orthoses 600. Moreover, Velcro structure 604 may further include connecting point 607 that may include a plastic material having a curved routing cavity for receiving support strap 608 (similar to that described with reference to FIG. 5B). The Velcro portion of material 606 may include an identifying mark (not shown) that may assist in applying a consistent amount of tension to support straps 608 in some implementations. In some implementations, the level of tension (and position of identifying mark) may be determined by a doctor or other skilled technician as opposed to being determined by the user themselves. Additionally, and similar to that described with reference to FIGS. 3A-3C, orthoses 500, 600 may include anchor points on the medial and/or lateral side of the foot and anchor points on the medial and/or lateral side of the leg in some implementations. Such embodiments, and depending upon the configuration chosen, may be utilized in order to provide a combination of dorsiflexion support, inversion support, eversion support, and/or rotation support for the user of orthoses 500, 600.

Figure 7A:
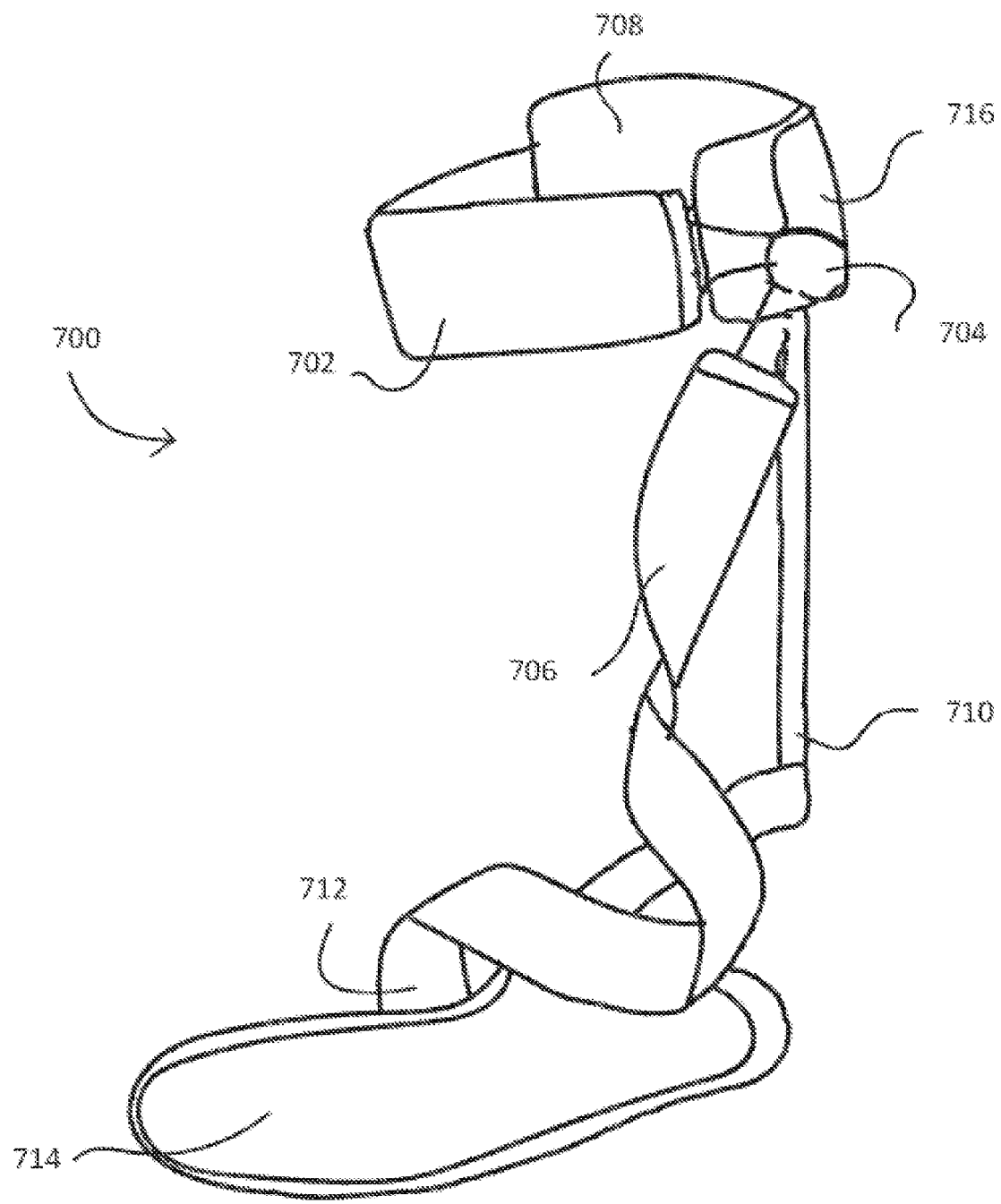
FIG. 7A is a perspective view of exemplary strapping that has been integrated into a rigid or semi-rigid AFO, in accordance with the principles of the present disclosure.
Figure 7B:
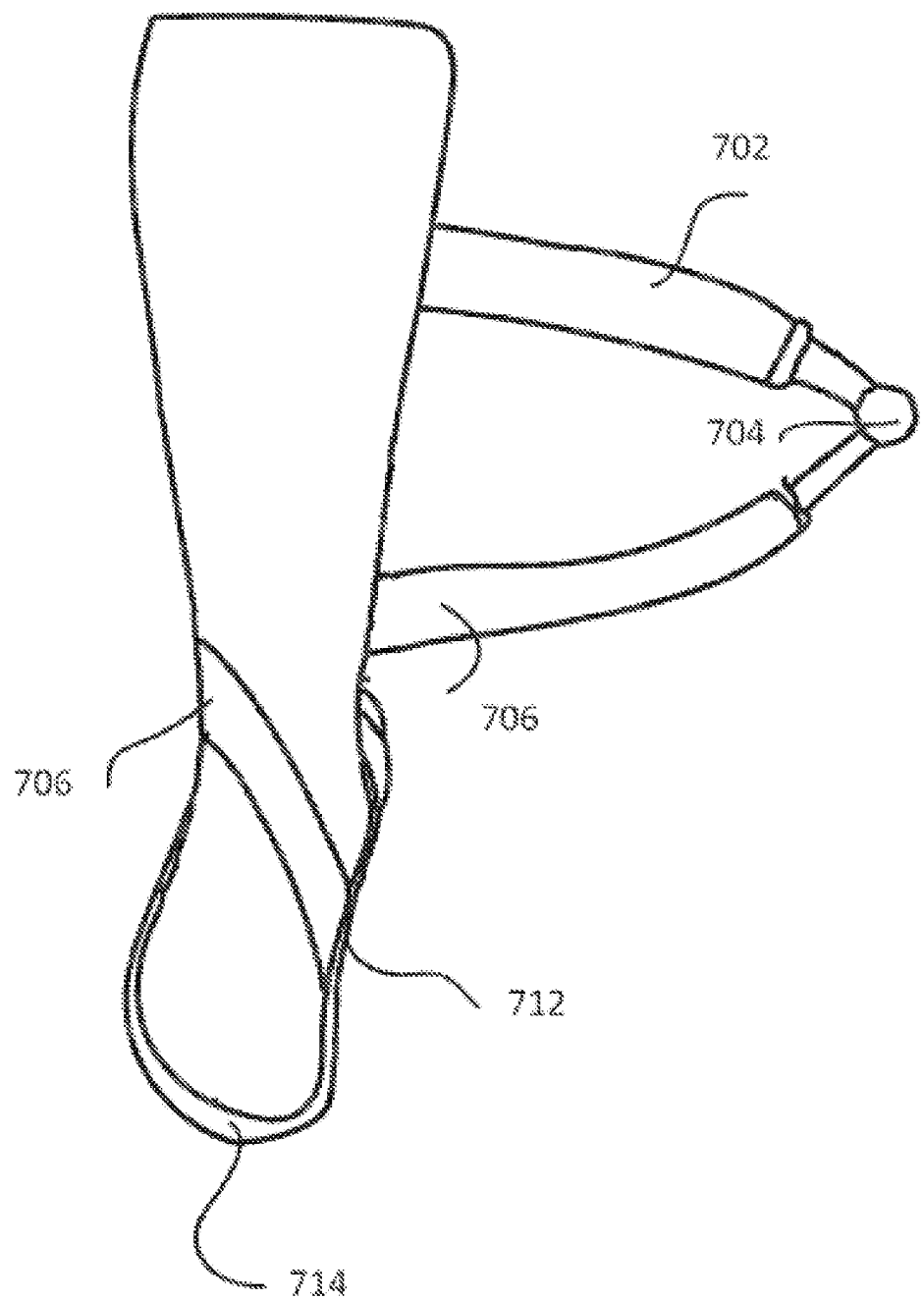
FIG. 7B is a front view of the exemplary strapping of FIG. 7A that has been integrated into a rigid or semi-rigid AFO, in accordance with the principles of the present disclosure.
Figure 7C:
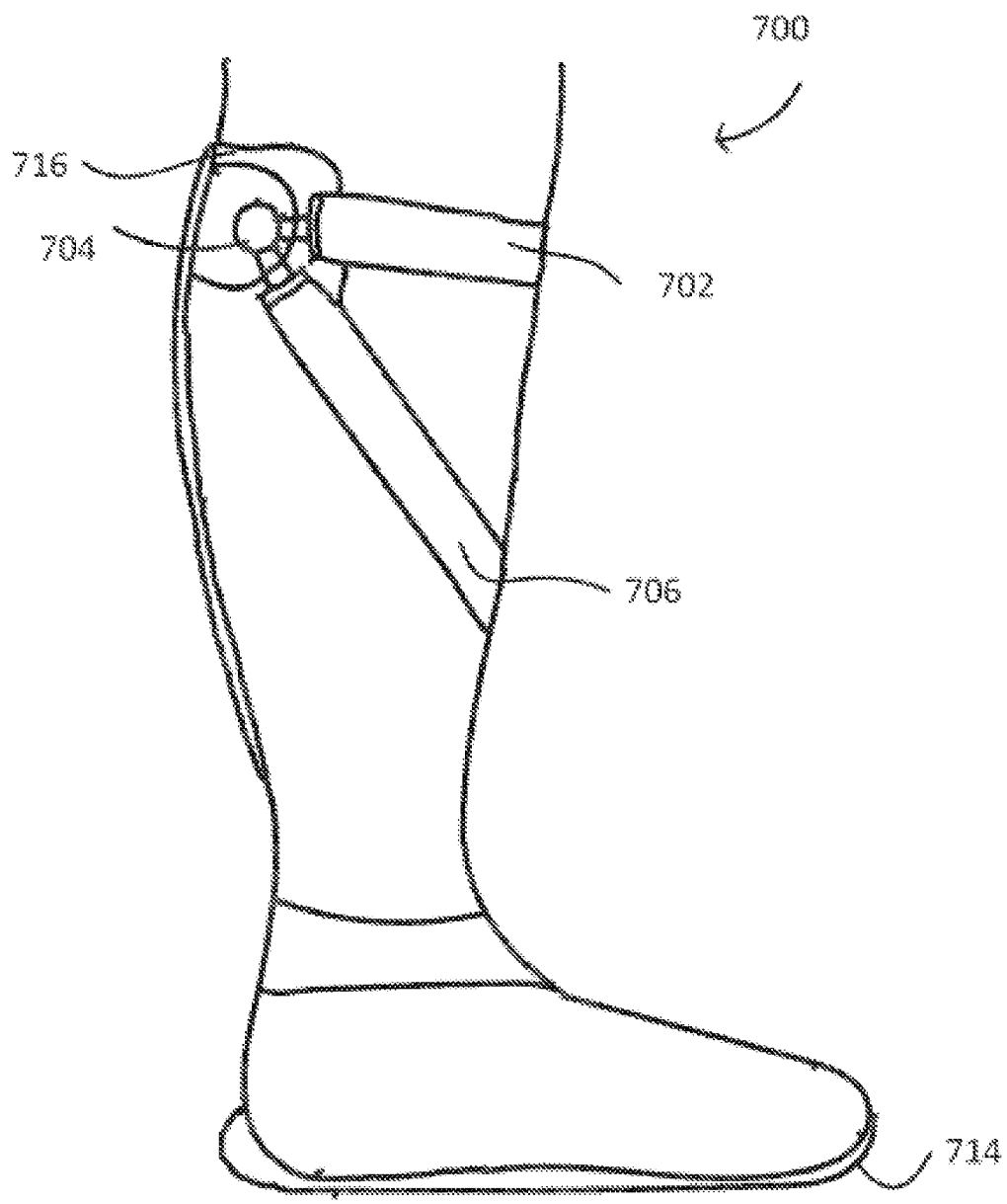
FIG. 7C is a side view of the exemplary strapping of FIG. 7A that has been integrated into a rigid or semi-rigid AFO, in accordance with the principles of the present disclosure.

Referring now to FIGS. 7A-7C, yet another foot ankle orthoses 700 is shown and described in detail. For example, FIG. 7A illustrates a rigid or semi-rigid AFO that includes a dynamic semi-flexible foot support section 714, an L-shaped frame 710 that is configured to be disposed around the foot and ankle and run up along a user's calf muscle, and a supporting structure 708 that is configured to fit adjacent to a user's knee. In some implementations, supporting structure 708 may be manufactured from a heat-moldable plastic, metal, leather, a carbon composite material, or various combinations of the foregoing. Support strap 706 may be anchored on the medial side of the foot in region 712, and further be anchored to a rotary tensioning system 704. Orthoses 700 may further include an adjustable strap 702 which may be secured to anchoring fabric 716 that is disposed on the supporting structure 708.

Referring now to FIG. 7B, orthoses 700 is shown being put on (or taken off) of the leg of a user. As can now more readily be seen, support strap 706 may be wrapped in a clock-wise direction around the lower leg of the user where both adjustable strap 706 and support strap 706 are attached to a rotary tensioning system 704. Accordingly, when rotary tensioning system 704 is secured to, for example, anchoring fabric (716, FIG. 7A), both adjustable strap 702 and support strap 706 may be simultaneously placed under tension through adjustments made through the rotary tensioning system 704. FIG. 7C illustrates orthoses 700 after an appropriate amount of tension has been applied via rotary tensioning system 704. The orthoses 700 as shown in FIGS. 7A-7C may include carbon fiber. Via inclusion of the support strap 706 (which may be either elastic or inelastic), an additional dorsiflexion support is provided, as well as inversion/eversion support dependent upon the direction of rotation for the support strap 706 and proper tibia alignment throughout the gait, similar to what a spiral carbon fiber orthoses would provide. Adding such a strap 706 onto this brace may add increased complexity of donning, however when configured with a rotary tensioning system 704 (e.g., a BOA dial) that allows for two (or more) straps to be adjusted at the same time, one can provide a greater level of function to the orthoses while simultaneously adding to the ease of donning and doffing.

Figure 8A:
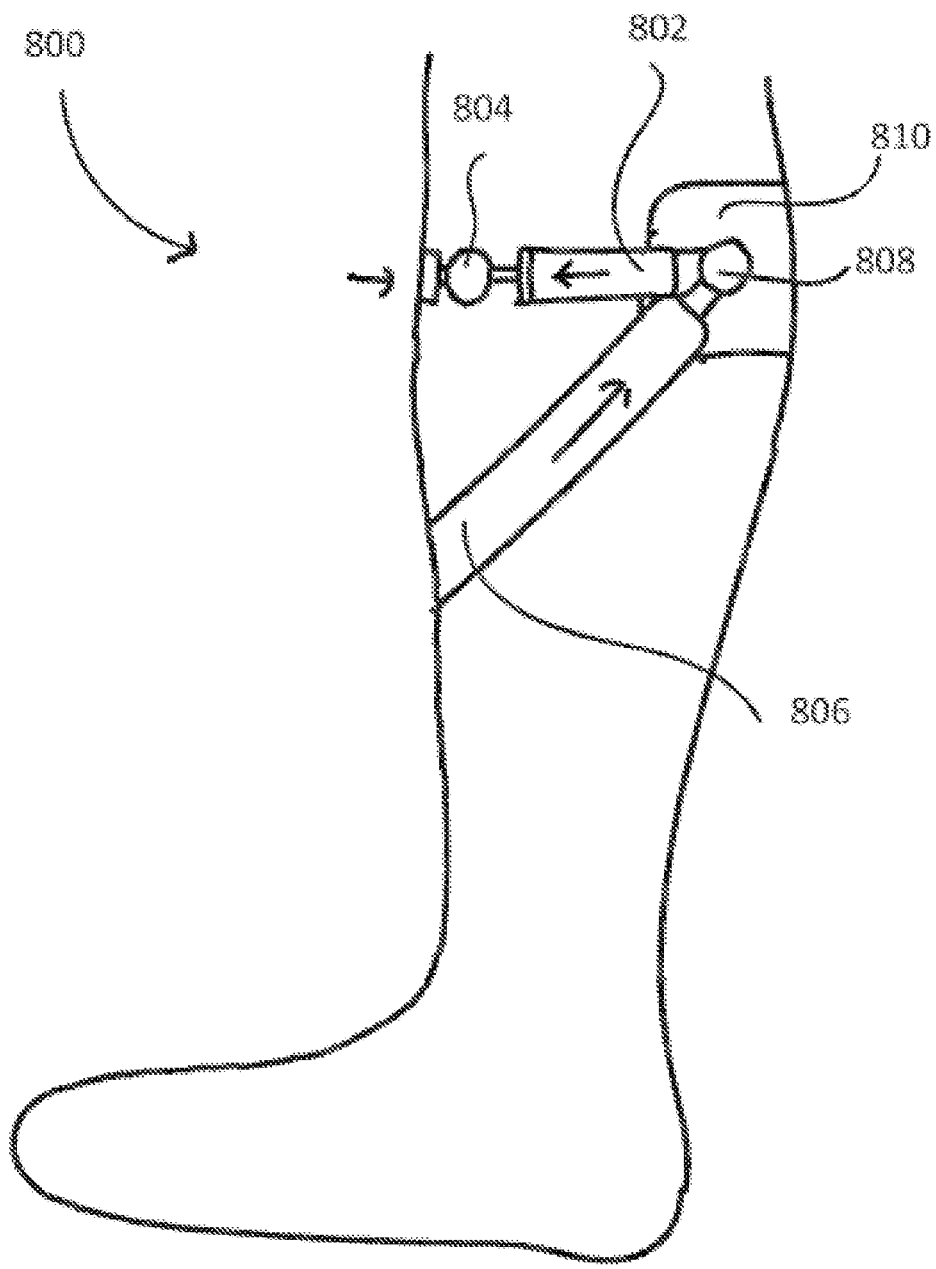
FIG. 8A is a side view of a first exemplary suspension strap and a dynamic loading strap that can be independently controlled using separate rotary tensioning systems, in accordance with the principles of the present disclosure.

Referring now to FIG. 8A, an alternative strapping configuration 800 is shown that may be utilized with one or more of the aforementioned orthoses described herein. In particular adjustable strap 802 may be placed under tension using rotary tensioning system 804, while support strap 806 may be placed under tension using a separate rotary tensioning system 808. Moreover, adjustable strap 802 and rotary tensioning system 808 may be removably (or fixedly) secured to supporting structure 810. In some implementations, these two straps may be mounted to the brace in the same (or similar) location thereby providing for the same ease of donning as described in, for example, FIG. 7B, but with a greater level of detailed adjustment per each strap.

Figure 8B:
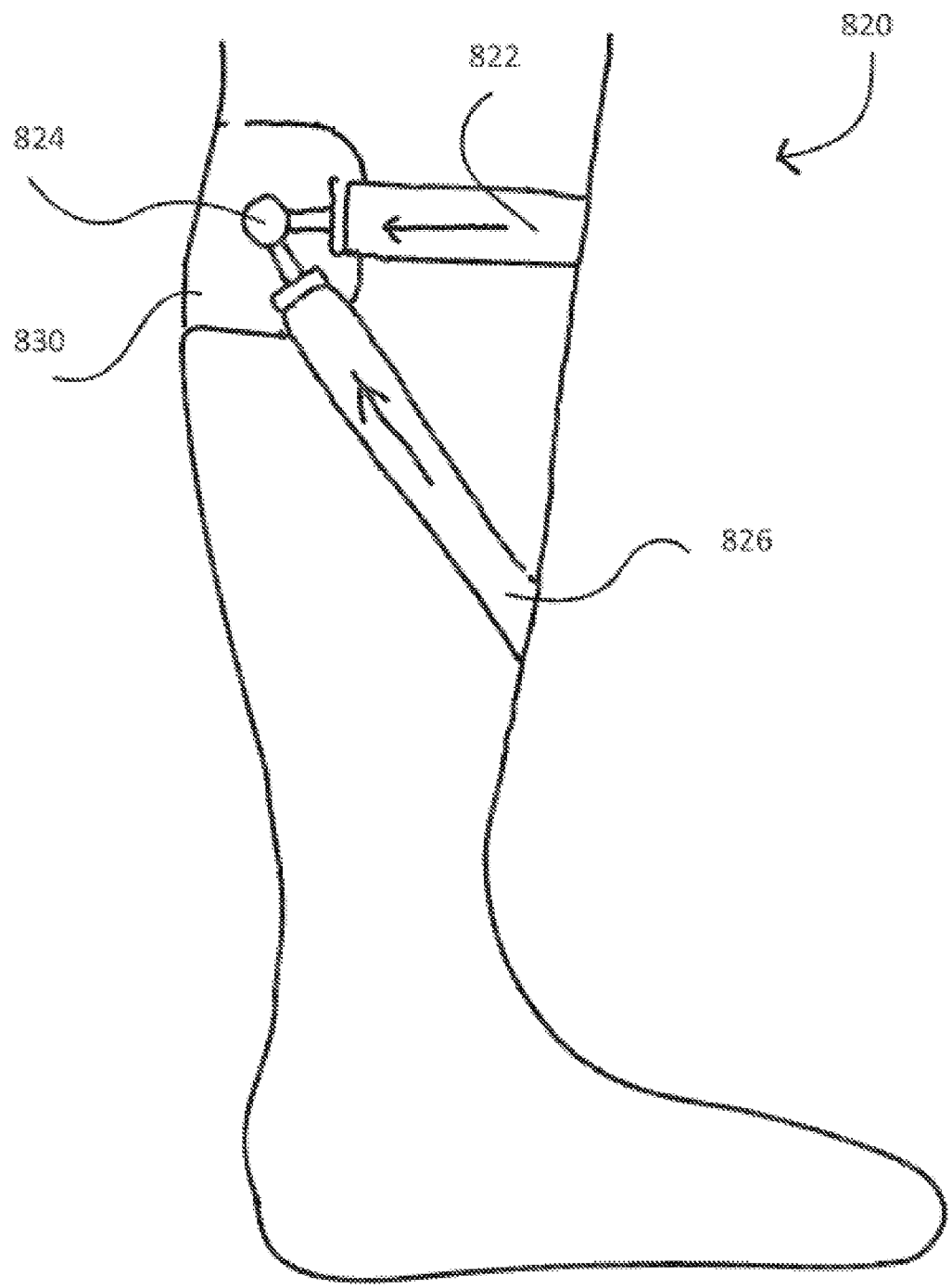
FIG. 8B is a side view of a second exemplary suspension strap and a dynamic loading strap that can be controlled using a common rotary tensioning system, in accordance with the principles of the present disclosure.

FIG. 8B illustrates yet another alternative strapping configuration 820 that may be utilized with one or more of the aforementioned orthoses described herein. In particular adjustable strap 822 may be placed under tension using rotary tensioning system 824, while support strap 826 may be simultaneously placed under tension using the same rotary tensioning system 824. Moreover, adjustable strap 822 and rotary tensioning system 824 may be removably (or fixedly) secured to supporting structure 830.

Figure 8C:
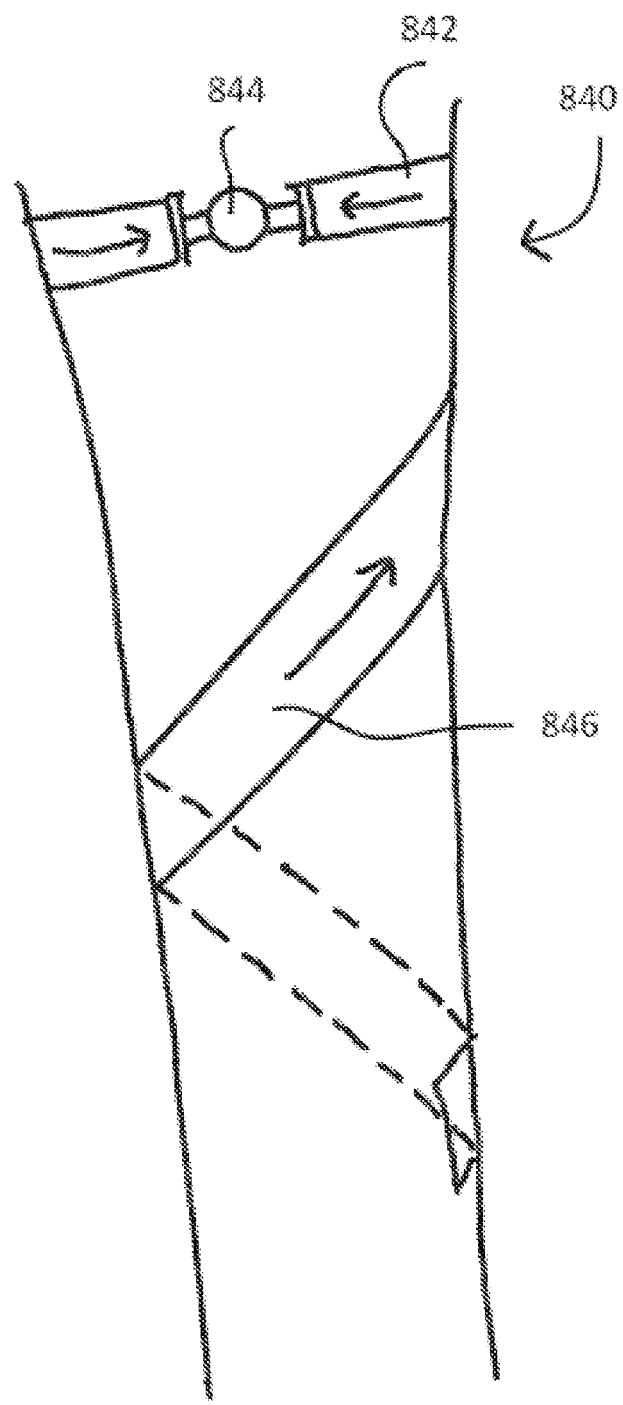
FIG. 8C is a back view of a third exemplary suspension strap and a dynamic loading strap that can be independently controlled using separate rotary tensioning systems, in accordance with the principles of the present disclosure.

FIG. 8C illustrates yet another alternative strapping configuration 840 that may be utilized with one or more of the aforementioned orthoses described herein. In particular adjustable strap 842 may be placed under tension using rotary tensioning system 844, while support strap 846 may be simultaneously placed under tension using another rotary tensioning system (not shown). For example, rotary tensioning system 844 may be placed on the front of the leg (e.g., near the top of the shin), while the other rotary tensioning system may be placed on the back side of the leg (e.g., near the top of the calf muscle).

Figure 8D:
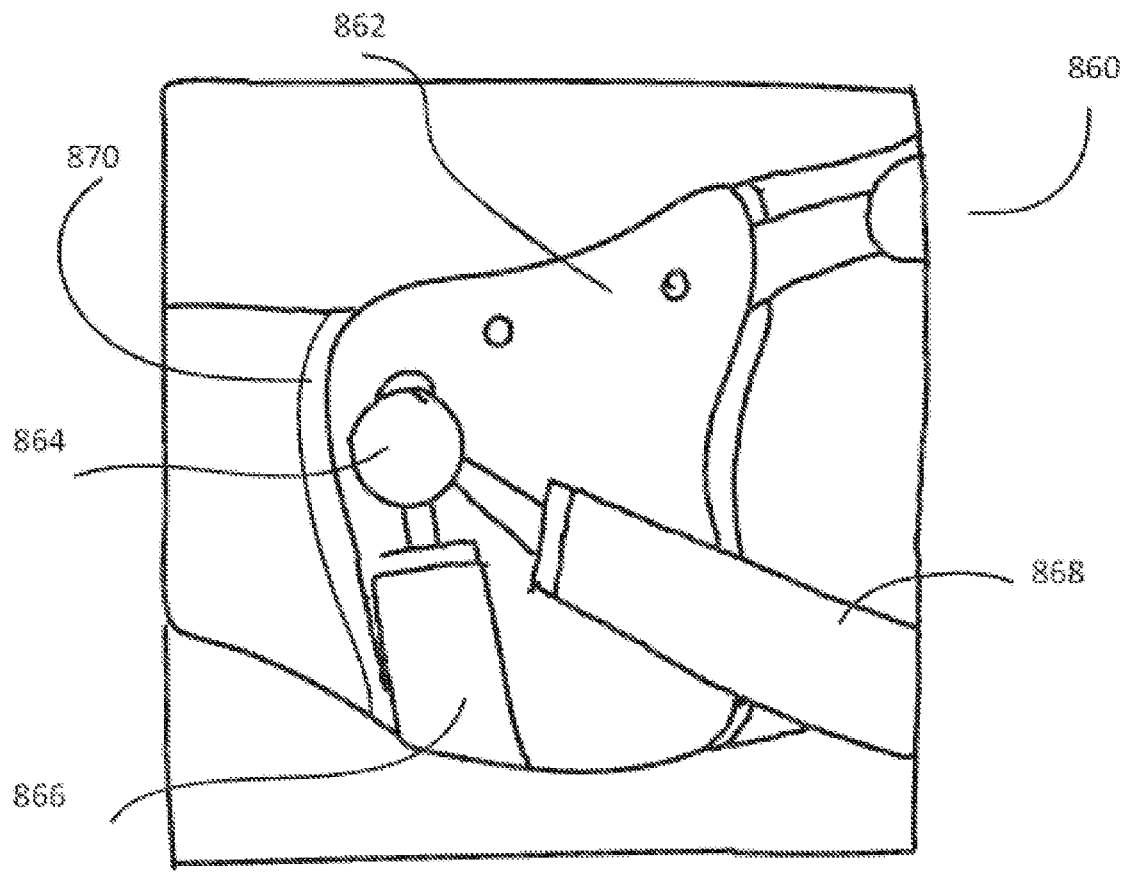
FIG. 8D is a perspective view of an exemplary double strapping system that has been integrated into a dynamic unloader, in accordance with the principles of the present disclosure.

FIG. 8D illustrates yet another alternative strapping configuration 870 that may be utilized with, for example, a knee brace 860 (such as, for example, the Unloader One® manufactured by Ossur). In the illustrated embodiment, the lower portion 862 of knee brace 860 may have a rotary tensioning system 864 disposed on the lateral side of the knee brace. The rotary tensioning system 864 may simultaneously apply tension around the calf muscle using adjustable strap 866 and support strap 868. The other end of the support strap 868 may be fixedly (or removably) secured to a top portion of the knee brace 860 on the medial side of the leg. Such a configuration may enable the underlying knee brace to laterally unload the knee. The top portion of the knee brace (not shown) may further include a thigh strap (not shown).

Moreover, while the rotary tensioning system 864 is illustrated as being disposed on the lateral side of the knee brace, it would be appreciated by one of ordinary skill given the contents of the present disclosure that the rotary tensioning system 864 may alternatively be placed on the medial side of the lower portion 862 of knee brace 860 with the support strap 868 spiraling up the leg with the opposing end secured to the thigh frame at the anterior/medial side. Such a configuration may enable the underlying knee brace to medially unload the knee. The rotary tensioning system 864 may simultaneously apply tension around the calf muscle using adjustable strap 866 and support strap 868.

Moreover, other dispositions of the rotary tensioning system 864 are readily envisaged given the contents of the present disclosure, including on the top of the leg (e.g., near the top of the shin), the back of the leg (e.g., near the top of the calf), or even on other dispositions on the top portion of knee brace 860. For example, in some implementations it may be desirable to include, for example, a first rotary tensioning system 864 disposed on the lateral (or medial) side of the lower portion 862 of the knee brace 860 with a first support strap 868 spiraling up the leg and being secured on the medial (or lateral) side of the top portion of the knee brace 860. Additionally, a second rotary tensioning system 864 may be disposed on the lateral (or medial) side of the top portion of the knee brace with a second support strap 868 spiraling down the leg (e.g., in an opposite direction to the first support strap 868) and being secured on the medial (or lateral) side of the lower portion 862 of the knee brace 1860. In some implementations, tightening of the first rotary tensioning system 864 may simultaneously tighten the first support strap 868 and adjustable strap 866 around the calf muscle, while tightening of the second rotary tensioning system 864 may simultaneously tighten the second support strap 868 and adjustable strap 866 around the thigh muscle. These and other variants would be readily apparent to one of ordinary skill given the contents of the present disclosure.

Figure 9A:
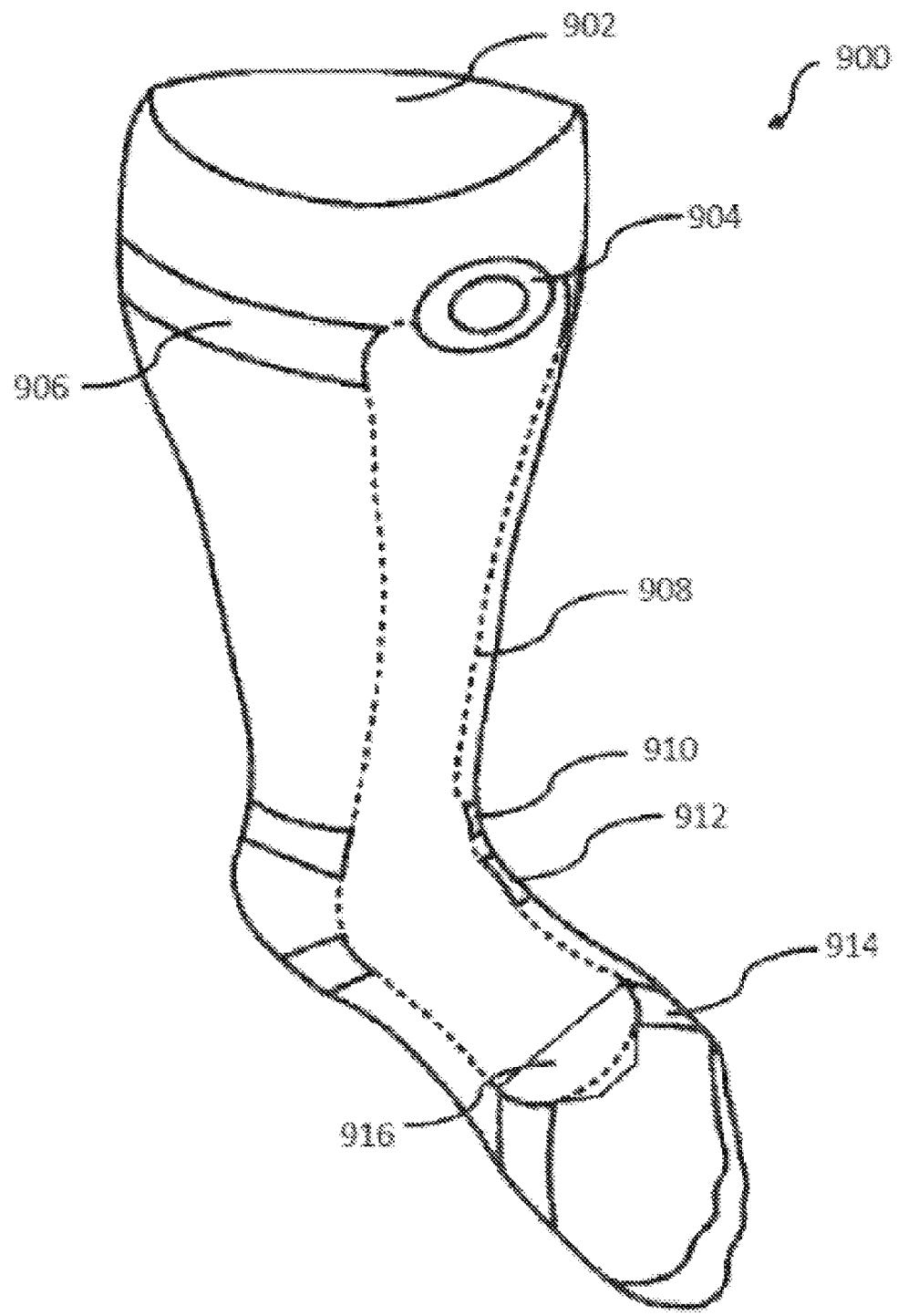
FIG. 9A is a front perspective view of yet another exemplary orthoses device that been integrated into a sock, in accordance with the principles of the present disclosure.
Figure 9B:
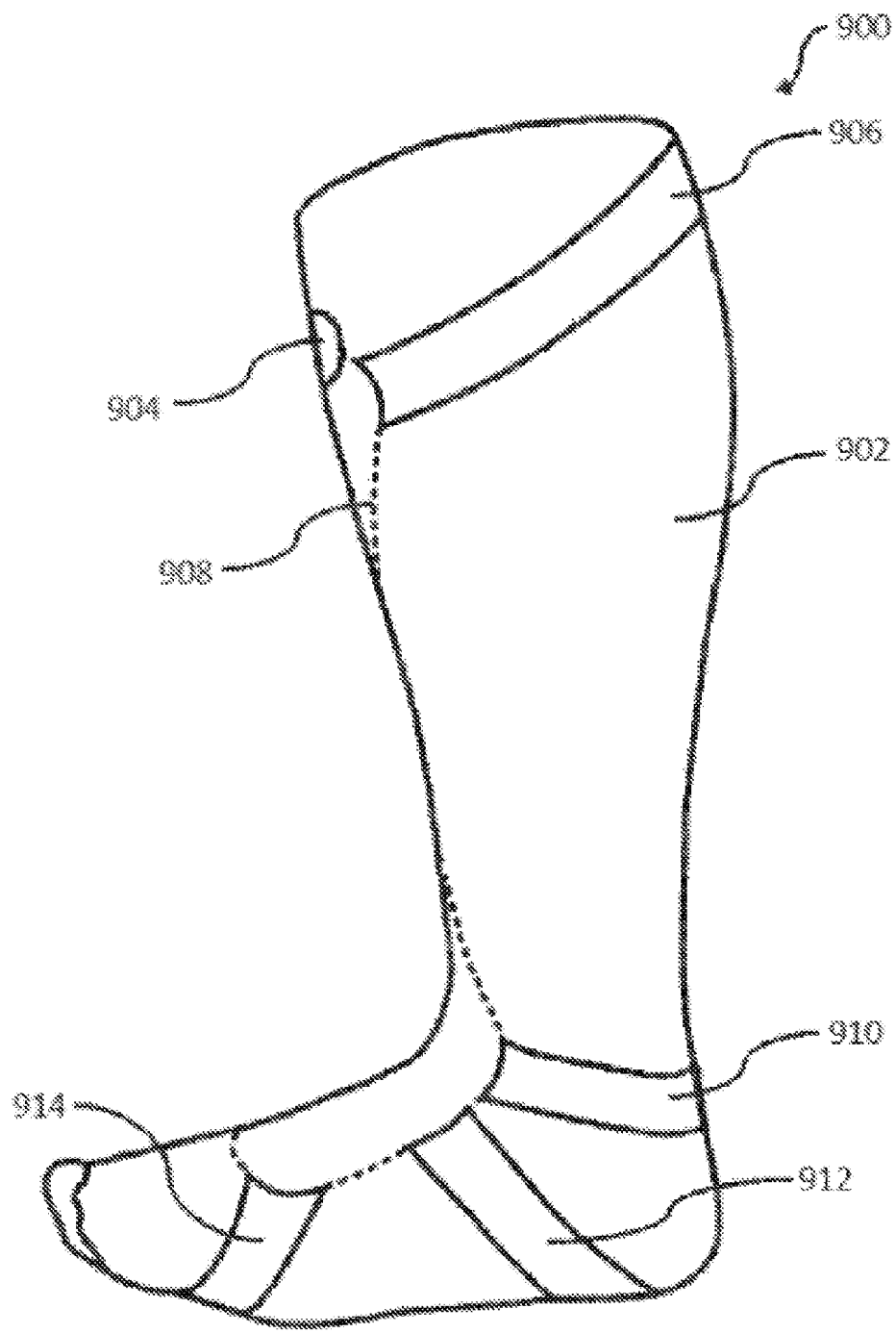
FIG. 9B is a side perspective view of the orthoses device shown in FIG. 9A, in accordance with the principles of the present disclosure.
Figure 9C:
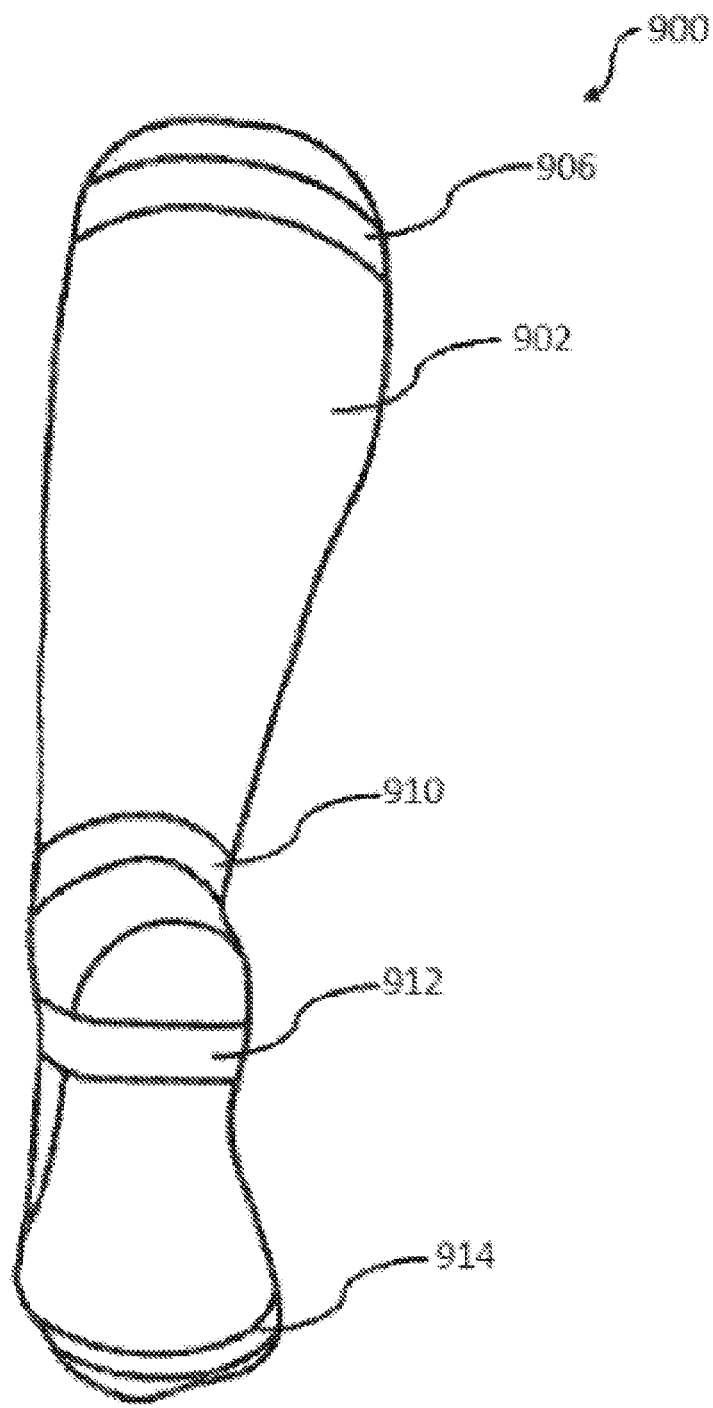
FIG. 9C is a back perspective view of the orthoses device shown in FIGS. 9A and 9B, in accordance with the principles of the present disclosure.

Referring now to FIGS. 9A-9C, yet another foot ankle orthoses 900 is shown and described in detail. In some implementations, orthoses 900 may be integrated into a sock 902 as illustrated. As illustrated, the sock may consist of an over the calf sock 902 (i.e., the sock is configured to reach over a wearer's calf muscle). However, in alternative implementations orthoses 900 may be distinct and separate from an underlying sock and may be utilized (or not utilized) in conjunction with a separate and distinct sock. For example, the compression strap system (e.g., retention straps 906, 910, 912, 914; support strap(s) (or cable(s)) 908; and rotary tensioning mechanism 904) may be separable from the sock 902 for the purposes of, for example, enabling the sock 902 to be cleaned independent from the compression strap system.

The foot ankle orthoses 900 may be utilized as an aid device for drop foot patients; however, such a means for utilization is not the only condition for which foot ankle orthoses 900 may be utilized. For example, foot ankle orthoses 900 may be used as a sleeve to control, for example, swelling/edema in a patient. Additionally, or alternatively, foot ankle orthoses may be utilized to serve as a proprioceptive reminder device in some implementations. For example, for a wearer of the foot ankle orthoses 900 who is dealing with an injury to the lower part of their leg, the foot ankle orthoses 900 may be used as an indicator that, for example, the wearer is over-exerting themselves during rehabilitation exercises as but one example. In other words, the pressure applied to the lower part of the leg by the foot ankle orthoses 900 may act as a reminder (e.g., such as an increase in pressure caused by swelling as but one example) to a wearer rehabilitating an injury, thereby promoting increased attention to the injury itself. Additionally, foot ankle orthoses 900 may help alleviate fatigue as; for example, the support strap(s) 908 (or cable(s)) are precisely tightened to predetermined (e.g., comfortable) specifications. These and other applications for the foot ankle orthoses 900 would be readily apparent to one of ordinary skill given the contents of the present disclosure.

The sock 902 (and/or compression strap system) may include features that allow for improved mating between the sock 902 and the compression strap system in implementations in which the sock 902 is separable from the compression strap system. For example, the sock 902 and/or compression strap system may include Velcro or other suitable means to removably couple the sock 902 with the compression strap system. The sock 902 may include integrated rubber beads to prevent, inter alia, movement of the sock 902, with respect to the user's leg and/or the compression strap system, when a wearer of the sock is in motion. These integrated rubber beads may be integrated within the sock (i.e., for contact against a wearer's skin) and/or may be integrated on an external portion of the sock (e.g., for contact with one or more straps of the compression strap system). In some implementations, these integrated rubber beads may be integrated within the compression strap system itself in addition to, or alternatively from, integrated rubber beads on the sock itself (whether internal, and/or external, to the sock 902).

In some implementations, orthoses 900 may include an upper retention structure 906, a rotatory tensioning mechanism 904 (such as, for example, the aforementioned BOA® tensioning system), support strap(s) (or cable(s)) 908, an upper ankle retention structure 910, a lower ankle retention structure 912, and a foot retention structure 914 which may be disposed adjacent to, for example, the ball of the foot (i.e., the padded portion of the sole of the foot between the toes and the arch). These retention structures 906, 910, 912, 914 may be manufactured from a same (or similar) underlying material, or may alternatively be manufactured from disparate materials. These materials may include, for example, fabrics, rubber-like materials, plastics, resins and/or synthetic materials. Additionally, these retention structures 906, 910, 912, 914 may be integrated with the sock 902 in, for example, inelastic knitting zones of the sock 902. These retention structures 906, 910, 912, 914 (or portions thereof) may also be integrated external to the sock (as illustrated), integrated internal to the sock 902 (i.e., between two or more layers of the underlying sock material) and/or integrated internal to all layer(s) of the sock 902.

The underlying sock 902 may, in some implementations, include low stretch in the horizontal direction at least in the region of the ankle and at the top of the calf (i.e., in the region of upper retention structure 906). The underlying sock may include a higher amount of stretch in the horizontal direction in one or more other regions so as to enable orthoses 900 to be put on, and taken off, easily, while also providing for improved comfort. Orthoses 900 may also include low stretch in the vertical direction to ensure proper stability of the dorsi flexion support strap/cable 908.

Moreover, in the illustrated embodiment, support strap 908 is shown as an inelastic cable that is threaded within the underlying sock so as to enable, inter alia, decreased visibility of the support strap 908. In some implementations, the support strap 908 (e.g., inelastic cable) may be threaded into the underside of sock (i.e., support strap 908 may be threaded so that portions thereof are disposed adjacent to, for example, the skin of a wearer of orthoses 900), while in other implementations the support strap 908 may be threaded inside of the sock such that the material of the sock is disposed between the skin of a wearer and the support strap 908 so as to mitigate irritation to the user's skin by support strap 908. In some implementations, it may be desirable to thread support strap 908 entirely within the sock. By virtue of the support strap 908 being threaded into (and out of) the underlying sock material (or within the underlying sock material), the support strap 908 may be placed proximate to the user's foot/leg when the support strap 908 is placed under tension via, for example, rotary tensioning mechanism 904. In other implementations (not shown), the support strap may be disposed entirely (or almost entirely) within the sock (or underneath the sock) for the purpose of making orthoses 900, inter alia, aesthetically pleasing. In yet other implementations, support strap 908 may be positioned external to the sock 902 and may be held in close proximity to the wearer by virtue of the interface portions of the support strap 908 with the retention structures 906, 910, 912, 914. Preferably, orthoses 900 may be utilized with a standard set of shoes, boots, etc., in some implementations.

Retention structures 906, 910, 912, 914 may integrate support strap/cable guides in some implementations at the point where the support strap/cable 908 interfaces with respective ones of the retention structures 906, 910, 912, 914. The purpose of these support strap/cable guides is to reduce friction and facilitate movement of the support strap/cable 908 as this support strap/cable is tightened (or loosened) with respect to the retention structures 906, 910, 912, 914. These support strap/cable guides may include one or more of lace guides that are manufactured from, for example, fabric, rubber, plastics, metals, resins and/or synthetics. In some implementations, one or more of these support strap/cable guides may include a pulley, hook, hollow rivet, etc. that may be utilized to guide the support strap/cable 908 during tightening (or loosening) operations.

These retention structures 906, 910, 912, 914 may be positioned at various strategic contours associated with the anatomy of the wearer. For example, upper retention structure 906 may be positioned above the calf of a wearer and below the knee, upper ankle retention structure 910 may be positioned below the calf and above the ankle, lower ankle retention structure 912 may be positioned below the ankle at a transition point between a wearers heel and the arch of the foot (i.e., at a transition point between the hind foot and the midfoot of a wearer), and foot retention structure may be positioned between the ball of a user's foot and the arch of the foot. In other words, positioning these retention structure(s) 906, 910, 912, 914 at areas of contour (e.g., portions of the anatomy that get "skinny") provides for improved anchor points for the compression strap system. In some implementations, various one(s) of these retention structures may be removed (e.g., lower ankle retention structure 912 and/or upper ankle retention structure 910, etc.). In some implementations, there may be a need for at least three of these retention structures (e.g., retention structure 906, retention structure 910 or 912, and retention structure 914) so as to properly provide sufficient support while maintaining the tensioning element in close proximity to the leg.

In some implementations, the compression strap system may be integrated onto other wearable support structures other than the foot ankle orthoses 900 explicitly shown. For example, in the context of an arm and elbow orthoses (not shown), retention structures may be placed above the bicep, above and/or below the elbow and at the wrist as but one exemplary example. As but another exemplary example in the context of a leg and knee orthoses, retention structures may be placed at the top of the thigh, above and/or below the knee and below the calf. In sum, various embodiments may be envisioned for use on various portions of the human anatomy with retention structures (e.g., anchor points) being positioned at various portions of the anatomy which go from either larger diameter to smaller diameter or from smaller diameter to larger diameter, etc. These and other variations would be readily apparent to one of ordinary skill given the contents of the present disclosure.

While the use of an exemplary rotary tensioning mechanism 904 is illustrated, it would be readily apparent to one of ordinary skill given the contents of the present disclosure that this mechanism 904 may be obviated in favor of alternatives (such as the exemplary alternatives disclosed herein). For example, the rotary tensioning mechanism 904 may be obviated in favor of the support structure 204 having support ring 206 as shown in FIG. 2. As but yet another example, the rotary tensioning mechanism 904 may be obviated in favor of the support structure 404 having an attachment point 406 as shown in FIG. 4A. In yet other envisioned variants, the rotary tensioning mechanism 904 may be obviated in favor of "shoe lace"-type configuration in which the cinching of the shoe lace provides both a tightening of each of the retention structures 904, 910, 912, 914 along with a simultaneous maintaining of the foot in a neutral to slight dorsiflexion thus limiting plantarflexion of the ankle. This shoe lace-type configuration may utilize, for example, a shoe lace, rubber, fabric, Velcro, rope, elastic bands, cords, and/or springs, etc. These and other variations would be readily apparent to one of ordinary skill given the contents of the present disclosure.

Referring to FIG. 9A in particular, and in some implementations, it may be desirable to utilize a reinforced structure 916 at the top portion of the foot in between, for example, the opposing ends of the foot retention structure 914. In particular, one purpose for this reinforced structure 916 may be to prevent the over tensioning of the support strap(s) (cable(s)) 908 in the region of the toes where the pressure is created in order to lift (support) the toes. In other words, in some implementations, it may be desirable to make this area of orthoses 900 a no (or low) tension zone around the periphery of the foot for the purpose of making the orthoses 900 more comfortable to wear. This reinforced structure 916 may consist of, for example, plastic, rubber, reinforced fabrics and/or metal. In some implementations, the reinforced structure may be custom shaped for a given users anatomy, thereby providing for additional comfort when wearing the orthoses 900. Additional support strap/cable guides (not shown) may be provided on additional portions at the top of the foot (and/or along the lower leg) in order to provide additional support and comfort for a user of orthoses 900. Additional padding (and/or support) may be provided underneath (or around) retention structure(s) 906, 910, 912 and/or 914 dependent upon particular user preference for the purpose of providing additional comfort. The underside of the foot may also include padded areas (e.g., via the addition of foam, fabric and/or rubber, etc.) for added comfort. The addition of these padded areas may help prevent the user from feeling excess tension as the retention structure(s) 906, 910, 912 and/or 914 are placed under tension and may also be configured for a particular user's preferences. It should be noted that at least in some implementations, when a user's ankle goes into plantar flexion, the strap(s) (cable(s)) 908 may in response tighten. When the strap(s) (cable(s)) 908 tightens it may have a tendency to want to pull the sock down the leg. Since the strap(s) (cable(s)) 908 is attached (threaded) through retention strap 906 that is positioned above the calf, it will have a tendency to want to "pull" on this retention strap 906, which in returns provides for a greater level of suspension as strap(s) (cable(s)) 908 tighten. Accordingly, this mechanism may be thought of as a dynamic suspension system that may be used on any of the retention straps as well as used for different joints for various other pathologies.

Referring now to FIGS. 10A-10I various unloading style braces that may include a wrap around sleeve, a single upright frame and a Y strap unloading feature is shown and described in detail. A single dynamic force strap is effective to unload the knee in a soft dynamic way, however it may tend to cause the brace to rotate around the leg. Some have designed around that by adding a second dynamic force strap however it creates more bulk in the popliteal region and therefore discomfort for the user as well as an increased complexity of donning and doffing. This Y strap configuration uses a standard dynamic force strap but then a second strap that connects to the dynamic force strap above the popliteal, spirals around the leg to the thigh shell on the opposite site of where the dynamic force strap connects to the shell and therefore resists the rotation forces without creating bulk or discomfort in the popliteal region.

An orthopaedic device may include a hinge attached to a thigh shell and a calf shell. Such frame may be attached to a sleeve that includes a first panel defining opposed first and second sides. A second panel has a first end secured to the first side of the first panel along a seam between the upper and lower corners of the seam, and a second end defining at least one flap securable to the second side of the first panel at a location site. A first strap has a first end secured to the first side of the first panel below the second panel. A second strap has a first end secured to the first side of the first panel below the second panel and overlays at least a portion of the first strap. A dynamic Y force strap helically extends between the upper and lower portions of the orthopeadic device and connects to the first panel. Such strap splits into a second strap around knee center which spirals in the opposite direction of the first end to attach on the opposite side of the first panel. Such an orthopeadic device may contain a height adjustment mechanism so that the frame could be lengthened or shortened without tools in order to accommodate different leg lengths.

Figure 10A:
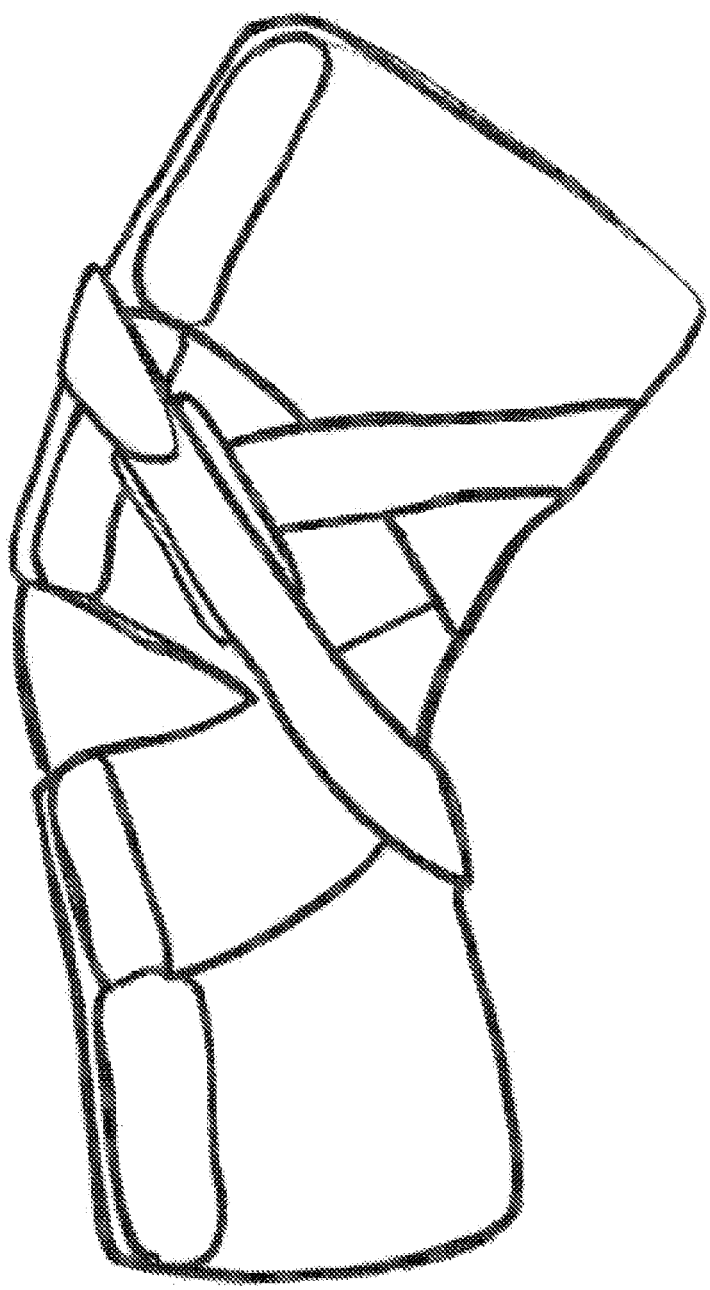
FIG. 10A is a front perspective view of yet another exemplary orthoses device with a Y Unloading strap shown on the lateral side of the device, in accordance with the principles of the present disclosure.
Figure 10B:
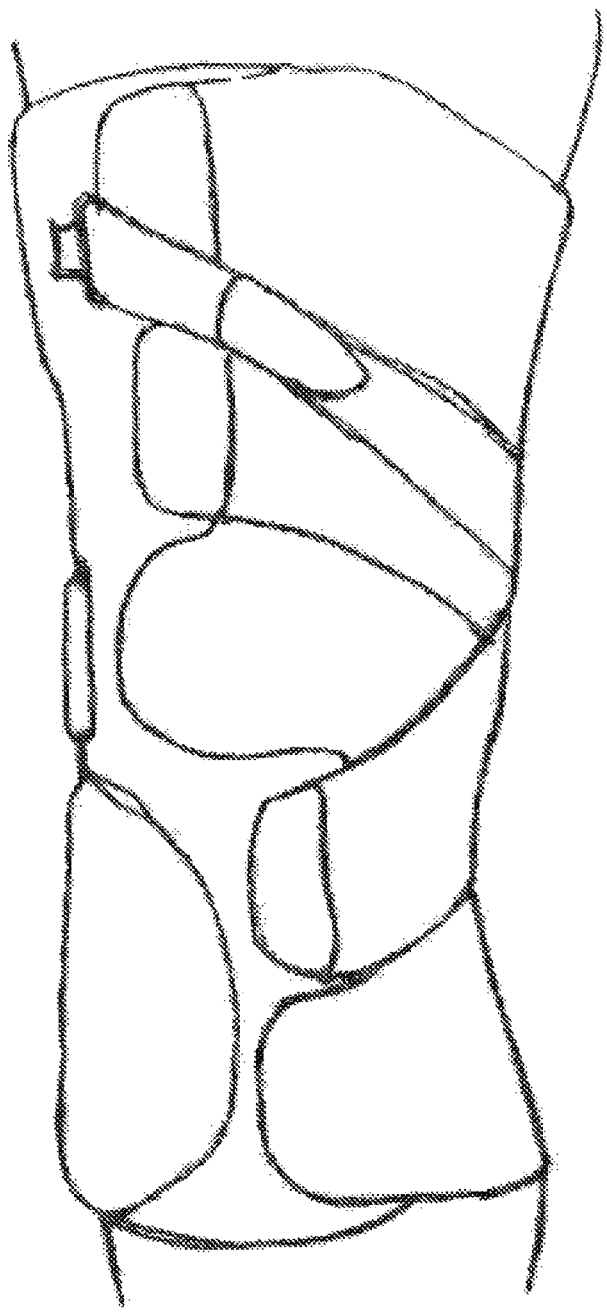
FIG. 10B is a front perspective view of the orthoses device of FIG. 10A shown on the front side of the device, in accordance with the principles of the present disclosure.
Figure 10C:
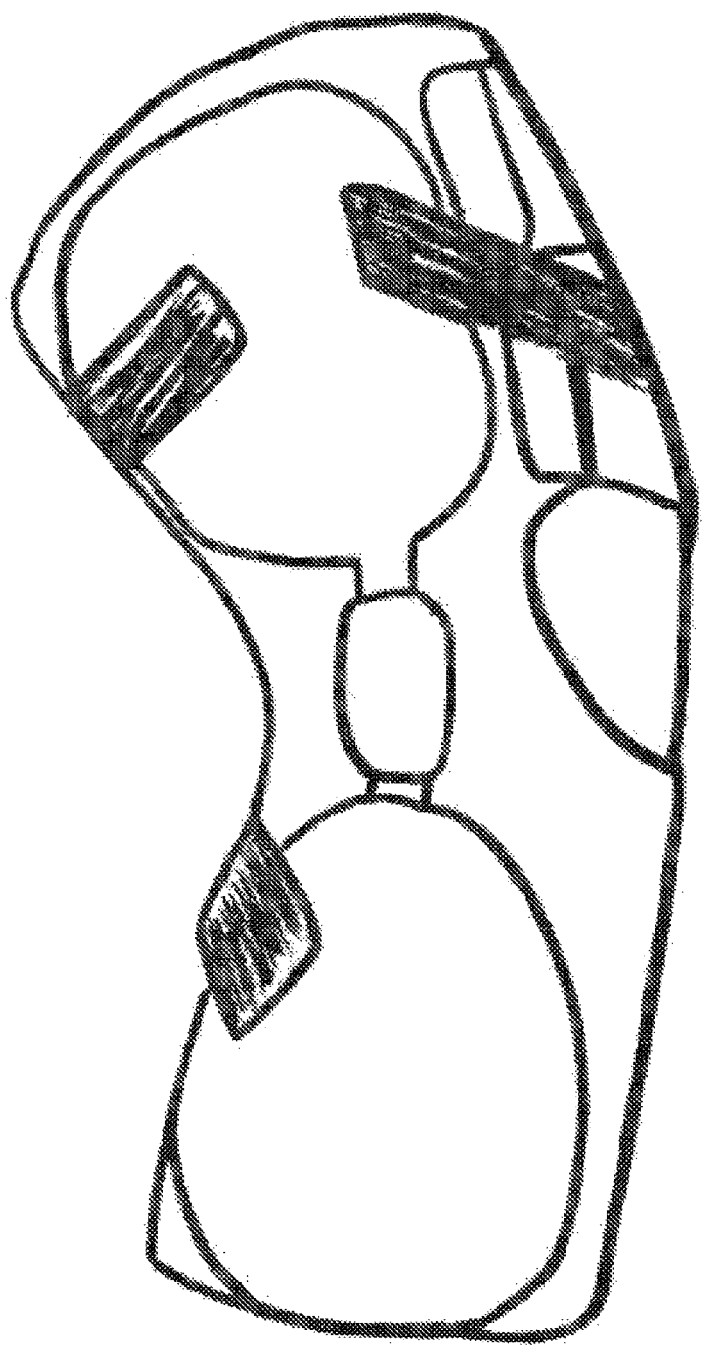
FIG. 10C is a front perspective view of the orthoses device of FIG. 10A shown on the medial side of the device, in accordance with the principles of the present disclosure.

FIGS. 10A-10C show the Y strap configuration using a Velcro connection. The so called half strap that creates the Y can be attached to the solid dynamic force strap using Velcro or any other means of attachment. In the current form a semi rigid or rigid plate is attached to the dynamic unloading strap with a keyhole. One end of the short strap may have a button hook sewn to it so that it may snap with the plate that is attached firmly to the dynamic unloading strap. This allows the short strap to pivot and align with the thigh to wrap around and attach to the thigh plate. Both strap ends attach to the thigh plate as can be seen on FIG. 10C. Both straps may be adjusted with a Velcro, Velcro through a D ring, BOA cable mechanism, ratchet, combinations of the foregoing or any other form of tightening mechanism.

Figure 10D:
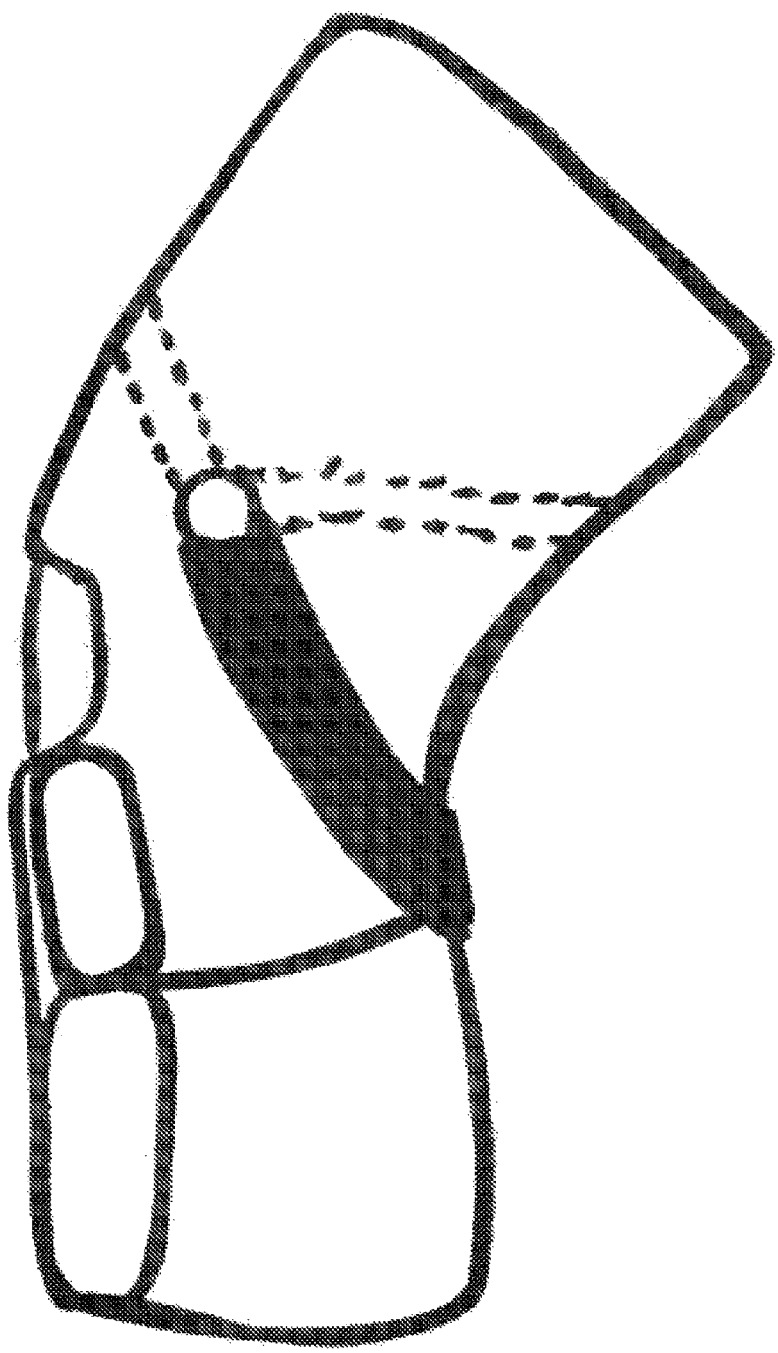
FIG. 10D is a side perspective view of yet another exemplary orthoses device with a Y Unloading strap from FIG. 10A using a BOA tensioning mechanism, in accordance with the principles of the present disclosure.
Figure 10E:
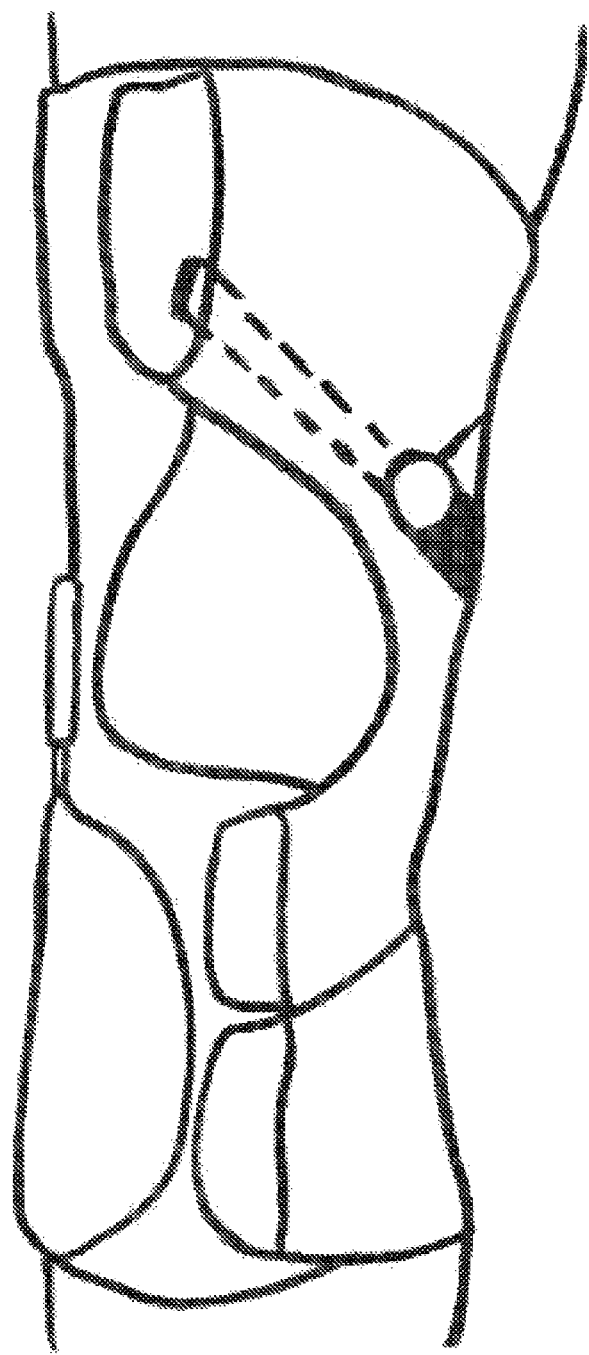
FIG. 10E is a front perspective view of the orthoses device of FIG. 10D on the front side of the device, in accordance with the principles of the present disclosure.

FIGS. 10D and 10E shows how the Y strap can be controlled with a single tensioning mechanism (e.g., a BOA mechanism). In this illustrated configuration, a single BOA dial or any other form of a tightening mechanism may be placed at the location where the strap separates into two straps. Cables may be embedded into the fabric of the sleeve or be visible and attached with guides on the outside of the sleeve. Offloading component may therefore be controlled through tightening of, for example, a single dial and all strap ends may be fixed to the frame (e.g., two at the thigh shell and one on the calf shell). There may additionally include an initial adjustment feature on both strap ends located on the thigh shell to ensure that the straps are adjusted enough to provide proper and even unloading when the tightening occurs.

Figure 10F:
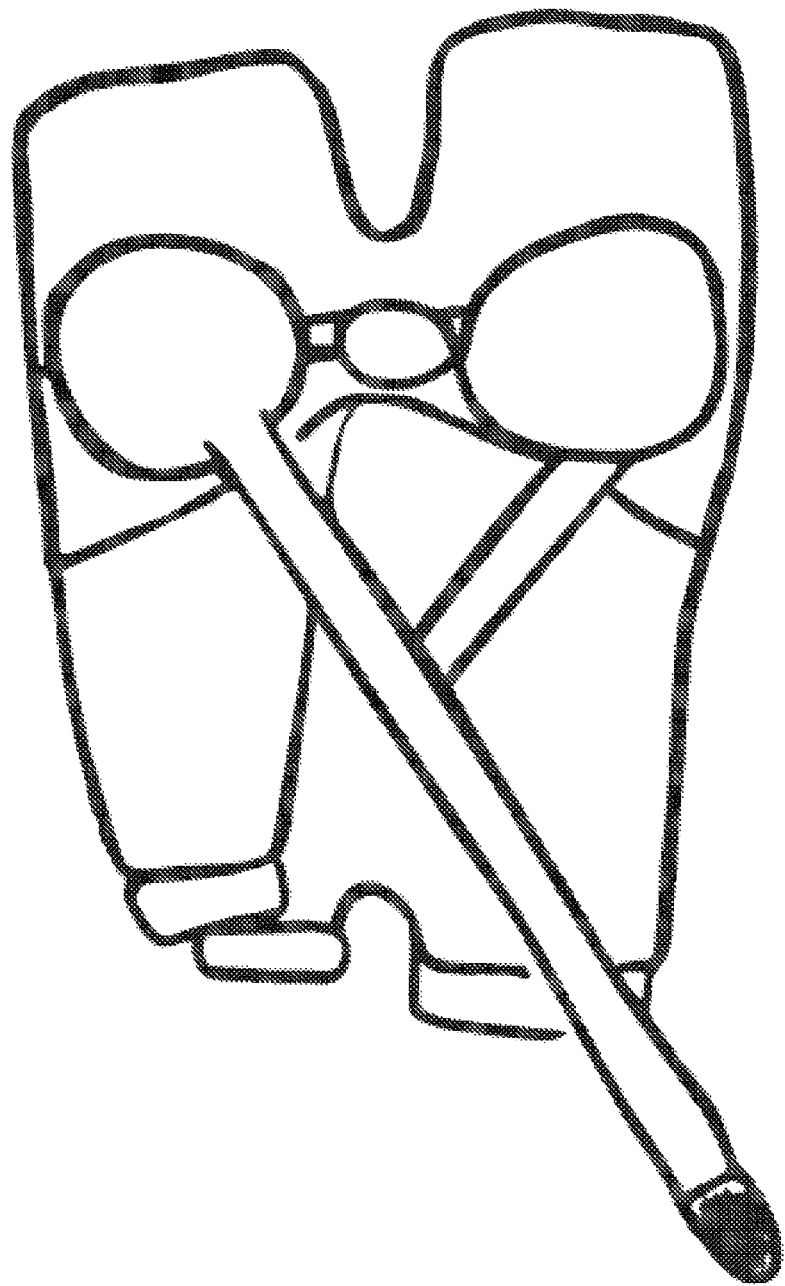
FIG. 10F is a flat view perspective of a sleeve used in the Y Unloading strap orthoses, in accordance with the principles of the present disclosure.
Figure 10G:
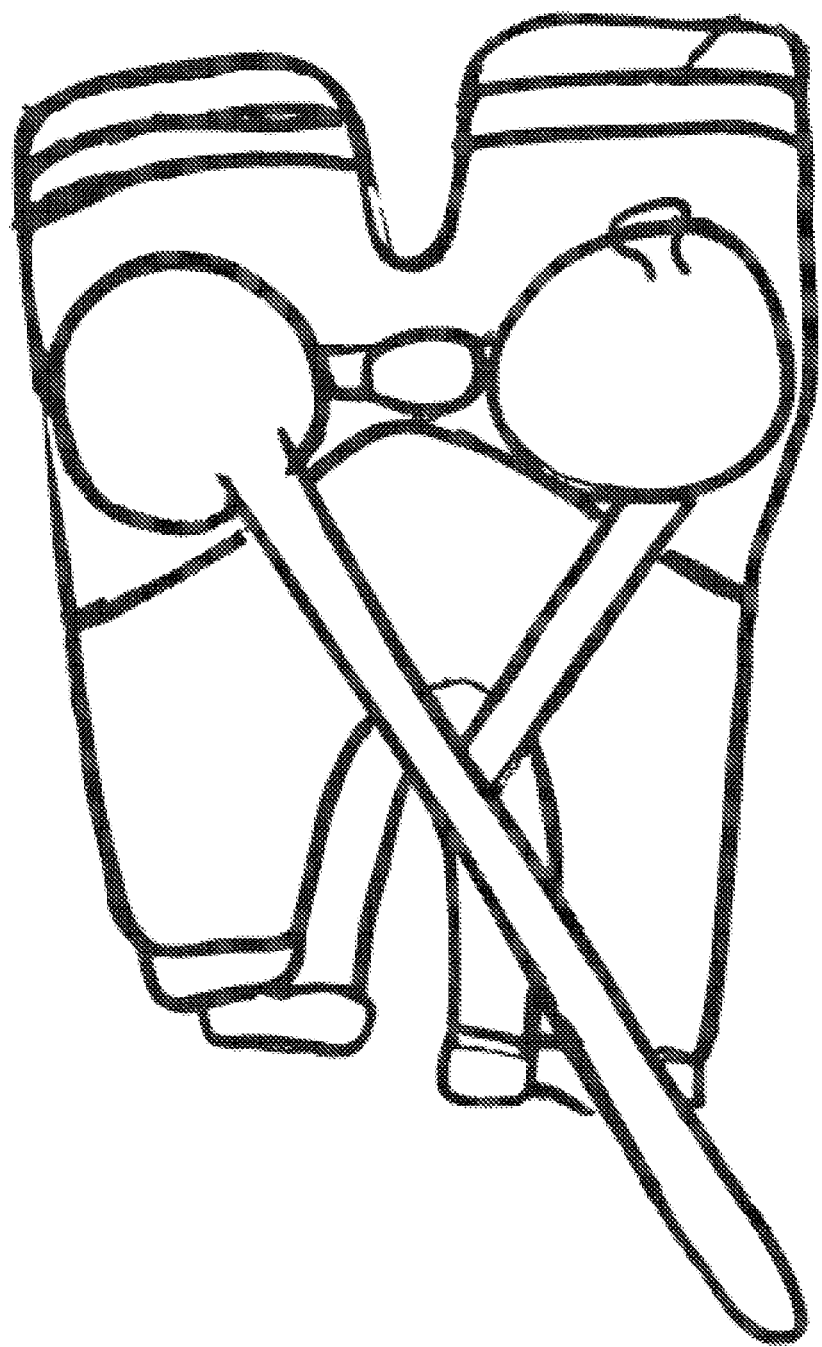
FIG. 10G is a flat view perspective of another sleeve configuration used in the Y Unloading strap orthoses (showing the gastric and the lower thigh underneath the panel), in accordance with the principles of the present disclosure.
Figure 10H:
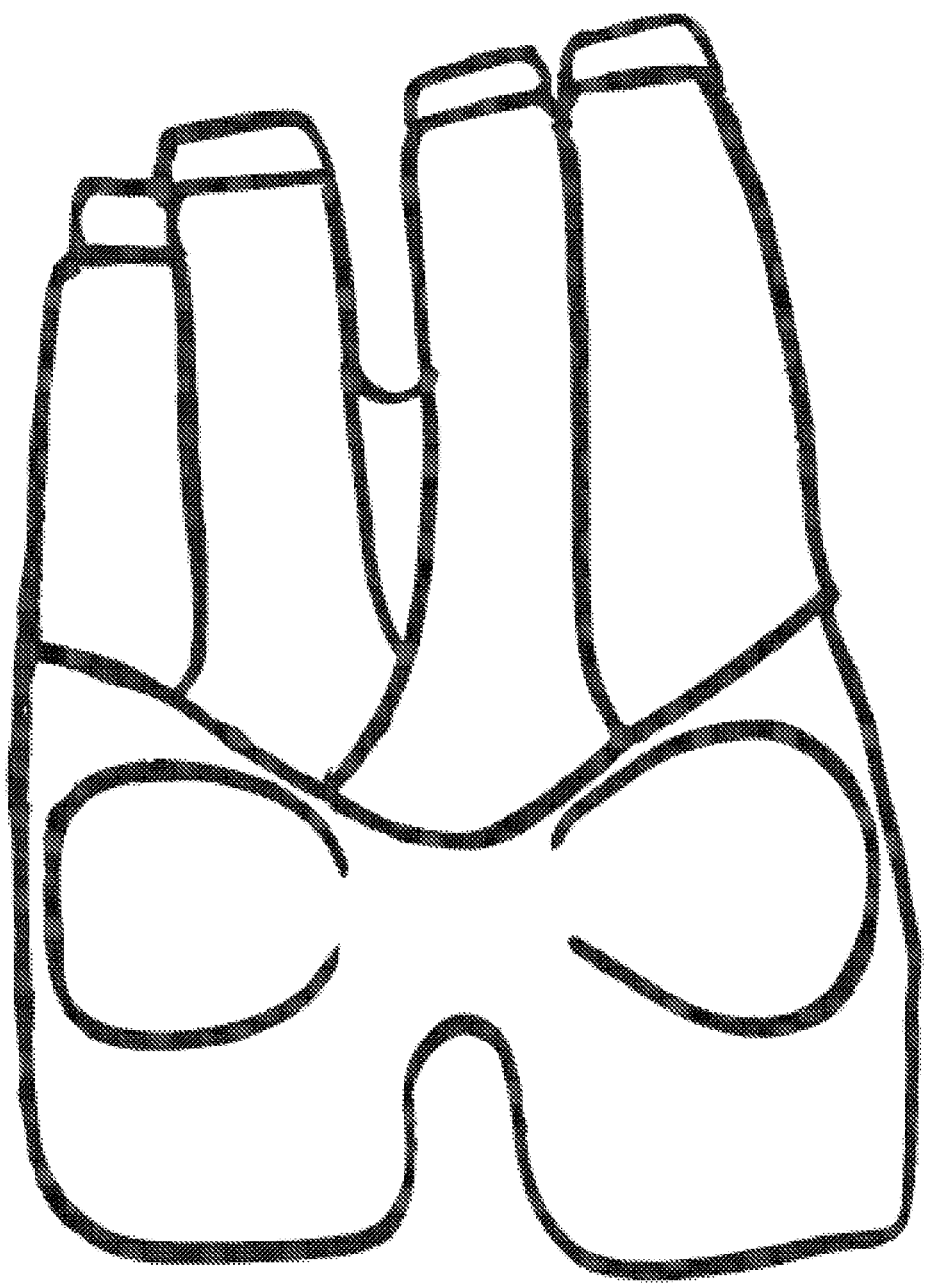
FIG. 10H is a flat view perspective of the configuration of FIG. 10G shown from the opposite side, in accordance with the principles of the present disclosure.

FIG. 10F-10H illustrates how the sleeve may be constructed using a wrap around sleeve configuration that includes three to four attachments respectively.

FIG. 10F shows a three tab configuration with a single wide tab at the thigh and two tabs on the calf. Such a configuration may aid the user with donning of the device, especially on the calf by providing, for example, a secure elastic suspension strap that is easy for the user to pull on. The number of steps required to don the brace may be fewer as compared to, for example, a four tab design.

FIG. 10G shows a flat view of the three tab configuration with one wide thigh flap that connects to the upper calf flap and then a separate lower calf strap which can either sit underneath or above the thigh/calf panel flaps. This lower calf strap could also be positioned as the upper calf strap to provide very secure suspension and sit underneath the thigh/calf flap. In that configuration the thigh/calf flap would consist of the thigh flap and the lower calf flap.

In FIG. 10G (an outer flat view), in this configuration the user starts by applying two straps, one above the calf and one on the lower thigh. Then patient applies a wide panel that includes the bottom calf attachment and the top thigh attachment. The two straps sit therefore underneath the wide outer panel. Prior to donning the brace fitter can use predetermined trim lines shown in order to adjust the brace to the appropriate circumference size for both thigh and calf. Another possible circumference adjustment is also through a wide alligator clip that can be added onto flap to lengthen brace circumference. Fitter can also alter the height of the brace by pushing buttons on thigh shell and calf shell that engage with arms on hinge to lengthen or shorten frame by pulling shells away from hinge center or pushing shells towards hinge center. Sleeve has sufficient vertical elasticity to accommodate the different frame lengths.

FIG. 10H shows the inner flat view of the brace shown in FIG. 10G.

Figure 10I:
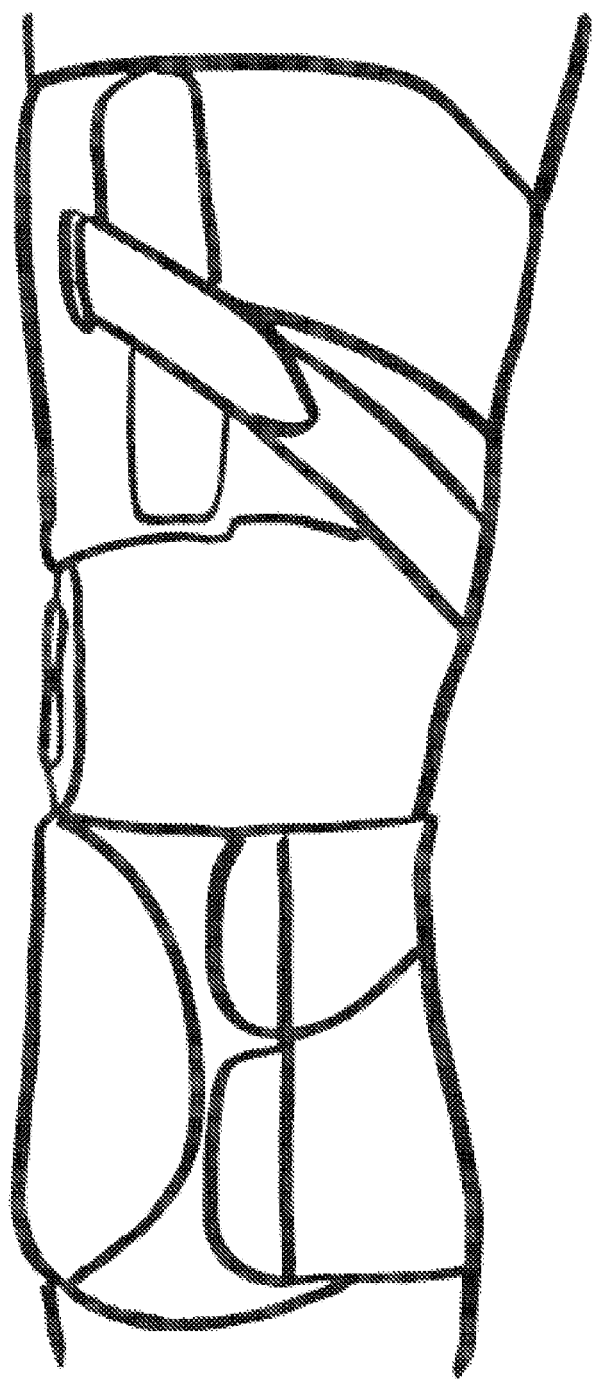
FIG. 10I is a front perspective view of the configuration shown in FIG. 10G and/or FIG. 10H in which the sleeve has been separated, in accordance with the principles of the present disclosure.

FIG. 10I shows two wraps, where one wrap is applied to a thigh shell and the other wrap is applied to a calf shell. Both wraps include two straps respectively to make sure that the donning is easy and effective in tension for the user. This provides a very secure suspension as well as comfortable compression above and below the joint. Another benefit of this system is that the brace frame could contain height adjustment for a short, regular and tall patient. The Y strap shown could also be a simple dynamic force strap without the additional Y strap component.

A similar Y strap configuration could also be applied to the lower section of the dynamic offloading strap, without the thigh strap component or in conjunction with the thigh component. When both straps were to be used with the offloading straps, rotational control applied to both thigh and calf can be accomplished. The two additional straps would both anchor to the offloading straps close to knee center however would not have to be anchored at the same location. This would allow for optimal placement of such straps without them having to cross in the popliteal which is a common issue for a so called double dynamic force strap brace. The lower strap section would then go through, for example, a D ring on the calf shell for tightening or adjustment by the patient similar to how the dynamic offloading strap is adjusted.

Where certain elements of these implementations can be partially or fully implemented using known components, only those portions of such known components that are necessary for an understanding of the present disclosure are described, and detailed descriptions of other portions of such known components are omitted so as not to obscure the disclosure.

In the present specification, an implementation showing a singular component should not be considered limiting; rather, the disclosure is intended to encompass other implementations including a plurality of the same component, and vice-versa, unless explicitly stated otherwise herein.

Further, the present disclosure encompasses present and future known equivalents to the components referred to herein by way of illustration.

It will be recognized that while certain aspects of the technology are described in terms of a specific sequence of steps of a method, these descriptions are only illustrative of the broader methods of the disclosure, and may be modified as required by the particular application. Certain steps may be rendered unnecessary or optional under certain circumstances. Additionally, certain steps or functionality may be added to the disclosed implementations, or the order of performance of two or more steps permuted. All such variations are considered to be encompassed within the disclosure disclosed and claimed herein.

While the above detailed description has shown, described, and pointed out novel features of the disclosure as applied to various implementations, it will be understood that various omissions, substitutions, and changes in the form and details of the device or process illustrated may be made by those skilled in the art without departing from the disclosure. The foregoing description is of the best mode presently contemplated of carrying out the principles of the disclosure. This description is in no way meant to be limiting, but rather should be taken as illustrative of the general principles of the technology. The scope of the disclosure should be determined with reference to the claims.

What is claimed:

1. A foot ankle orthosis, comprising:
a sock, the sock comprising two or more layers of material; and
a compression strap system that is at least partly integrated within the two or more layers of material of the sock, the compression strap system comprising:
an adjustable tensioning mechanism disposed on the sock, the adjustable tensioning mechanism configured to tension a cable;
an upper retention structure that is positioned proximate the adjustable tensioning mechanism;
an upper ankle retention structure that is positioned between the upper retention structure and a toe region of the sock, the upper ankle retention structure being integrated internal to the two or more layers of material of the sock, the upper ankle retention structure further comprising cable guides that interface with the cable internal to the two or more layers of material of the sock;
a lower ankle retention structure that is configured to be positioned between the upper ankle retention structure and the toe region of the sock, the lower ankle retention structure being integrated internal to the two or more layers of material of the sock, the lower ankle retention structure further comprising cable guides that interface with the cable internal to the two or more layers of material of the sock; and
a foot retention structure that is configured to be positioned between the lower ankle retention structure and the toe region of the sock, the foot retention structure further comprising cable guides that interface with the cable, the cable guides of the foot retention structure being integrated at a dorsal portion of the sock.

2. The foot ankle orthosis of claim 1, wherein the upper retention structure is configured to tighten around an anatomy of a user of the foot ankle orthoses when: (i) the adjustable tensioning mechanism is tightened and/or (ii) a foot of the user goes into plantar flexion.

3. The foot ankle orthosis of claim 2, wherein the upper ankle retention structure and the lower ankle retention structure are configured to tighten around the anatomy of the user of the foot ankle orthoses when the adjustable tensioning mechanism is tightened.

4. The foot ankle orthosis of claim 3, wherein the foot retention structure is configured to place the foot of the user into a neutral to slight dorsiflexion when the adjustable tensioning mechanism is tightened.

5. The foot ankle orthosis of claim 1, wherein the sock includes low stretch in a horizontal direction at least in a region between the upper ankle retention structure and the lower ankle retention structure and in a region adjacent the upper retention structure as compared with at least one other region of the sock.

6. The foot ankle orthosis of claim 1, wherein the cable comprises a substantially inelastic material.

7. The foot ankle orthosis of claim 6, wherein the cable is threaded into and out of at least one of the two or more layers of material of the sock.

8. The foot ankle orthosis of claim 6, wherein the cable is threaded between at least two of the two or more layers of material thereby preventing direct contact of the cable with skin of a user of the foot ankle orthoses.

9. The foot ankle orthosis of claim 6, further comprising a reinforced structure that is configured to prevent over tensioning of the cable in a region of a foot of a user of the foot ankle orthoses.

10. The foot ankle orthosis of claim 1, wherein the adjustable tensioning mechanism comprises a rotary tensioning mechanism.

11. The foot ankle orthosis of claim 10, wherein the cable guides of the lower ankle retention structure are integrated at an upper portion of the sock opposite from a sole region of the sock.

12. The foot ankle orthosis of claim 11, wherein the cable comprises a substantially inelastic material.

13. The foot ankle orthosis of claim 12, wherein the cable is threaded into and out of at least one of the two or more layers of material of the sock.

14. The foot ankle orthosis of claim 13, wherein the cable is threaded between at least two of the two or more layers of material thereby preventing direct contact of the cable with skin of a user of the foot ankle orthoses.

15. The foot ankle orthosis of claim 14, wherein the cable runs between the rotary tensioning mechanism and the foot retention structure.

16. A foot ankle orthosis, comprising:
a sock comprising two or more layers of material; and
a compression strap system that is at least partly integrated within the two or more layers of material of the sock, the compression strap system comprising:
an adjustable tensioning mechanism disposed on the sock, the adjustable tensioning mechanism configured to tension a cable;
an upper retention structure that is positioned proximate the adjustable tensioning mechanism;
an upper ankle retention structure that is positioned between the upper retention structure and a toe region of the sock, the upper ankle retention structure being integrated internal to the two or more layers of material of the sock;
a lower ankle retention structure that is configured to be positioned between the upper ankle retention structure and the toe region of the sock, the lower ankle retention structure being integrated internal to the two or more layers of material of the sock; and
a foot retention structure that is configured to be positioned between the lower ankle retention structure and the toe region of the sock;
wherein the cable is integrated within at least a portion of the two or more layers of material of the sock at least between the upper ankle retention structure and the foot retention structure to maintain the cable in proximity to a leg of a user.

17. The foot ankle orthosis of claim 16, wherein the cable runs between the adjustable tensioning mechanism and the foot retention structure.

18. The foot ankle orthosis of claim 17, wherein the cable comprises a substantially inelastic material.

19. The foot ankle orthosis of claim 18, wherein the cable is threaded into and out of at least one of the two or more layers of material of the sock.

20. The foot ankle orthosis of claim 19, wherein the cable is threaded between at least two of the two or more layers of material thereby preventing direct contact of the cable with skin of a user of the foot ankle orthoses.

* * * * *